United States Patent
Patel et al.

(10) Patent No.: US 10,575,767 B2
(45) Date of Patent: Mar. 3, 2020

(54) METHOD FOR MONITORING AN ANALYTE, ANALYTE SENSOR AND ANALYTE MONITORING APPARATUS

(71) Applicant: MEDTRONIC MINIMED, INC., Northridge, CA (US)

(72) Inventors: Anuj M. Patel, Sherman Oaks, CA (US); Zachary Decke, Van Nuys, CA (US); Bradley C. Liang, Bloomfield Hills, MI (US)

(73) Assignee: Medtronic MiniMed, Inc., Northridge, CA (US)

( * ) Notice: Subject to any disclaimer, the term of this patent is extended or adjusted under 35 U.S.C. 154(b) by 674 days.

(21) Appl. No.: 14/726,224

(22) Filed: May 29, 2015

(65) Prior Publication Data

US 2016/0345873 A1 Dec. 1, 2016

(51) Int. Cl.
*A61B 5/1473* (2006.01)
*A61B 5/145* (2006.01)
(Continued)

(52) U.S. Cl.
CPC .......... *A61B 5/1473* (2013.01); *A61B 5/1451* (2013.01); *A61B 5/14532* (2013.01);
(Continued)

(58) Field of Classification Search
USPC ....................................................... 600/345
See application file for complete search history.

(56) References Cited

U.S. PATENT DOCUMENTS 3,631,847 A 1/1972 Hobbs, II
4,212,738 A 7/1980 Henne
(Continued)

FOREIGN PATENT DOCUMENTS

DE 4329229 3/1995
EP 0319268 11/1988
(Continued)

OTHER PUBLICATIONS

Greet Van Den Berghe, M.D., Ph.D., et al., Intensive Insulin Therapy in Critically Ill Patients, The New England Journal of Medicine, Nov. 8, 2001, pp. 1359-1367, vol. 345, No. 19, Massachusetts Medical Society, USA.
(Continued)

*Primary Examiner* — Christian Jang
*Assistant Examiner* — Mitchell E Alter
(74) *Attorney, Agent, or Firm* — Lorenz & Kopf, LLP

(57) ABSTRACT

A method for monitoring an analyte within the body of a patient, an analyst sensor, and an analyte monitoring apparatus are presented here. In accordance with certain embodiments, the method for monitoring an analyte within the body of a patient includes implanting an analyte sensor at a sensor placement site in the patient. The analyte sensor includes a reference electrode, a counter electrode, a primary working electrode having a first structure, and an auxiliary working electrode having a second structure different from the first structure. The method includes communicating a primary signal from the primary working electrode and an auxiliary signal from the auxiliary working electrode to a processor. Further, the method includes monitoring the primary signal and the auxiliary signal with the processor to characterize a change in a physiological characteristic at the sensor placement site.

12 Claims, 13 Drawing Sheets

(51) Int. Cl.
    *A61M 5/142*      (2006.01)
    *A61B 5/1486*     (2006.01)
    *A61B 5/00*       (2006.01)

(52) U.S. Cl.
    CPC ............ *A61M 5/142* (2013.01); *A61B 5/145* (2013.01); *A61B 5/1486* (2013.01); *A61B 5/14865* (2013.01); *A61B 5/4839* (2013.01); *A61M 2230/201* (2013.01)

(56) References Cited

U.S. PATENT DOCUMENTS

| | | |
|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | Decant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutre et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutre et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,482,473 A | 1/1996 | Lord et al. |
| 5,485,408 A | 1/1996 | Blomquist |
| 5,505,709 A | 4/1996 | Funderburk et al. |
| 5,497,772 A | 5/1996 | Schulman et al. |
| 5,543,326 A | 8/1996 | Heller et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Illiff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutre et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,754,111 A | 5/1998 | Garcia |
| 5,764,159 A | 6/1998 | Neftel |
| 5,772,635 A | 6/1998 | Dastur et al. |
| 5,779,665 A | 7/1998 | Mastrototaro et al. |
| 5,788,669 A | 8/1998 | Peterson |
| 5,791,344 A | 8/1998 | Schulman et al. |
| 5,800,420 A | 9/1998 | Gross et al. |
| 5,807,336 A | 9/1998 | Russo et al. |
| 5,814,015 A | 9/1998 | Gargano et al. |
| 5,822,715 A | 10/1998 | Worthington et al. |
| 5,832,448 A | 11/1998 | Brown |
| 5,840,020 A | 11/1998 | Heinonen et al. |
| 5,861,018 A | 1/1999 | Feierbach et al. |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,978,236 A | 11/1999 | Faberman et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 | 1/2001 | Say et al. |
| 6,183,412 B1 | 2/2001 | Benkowski et al. |
| 6,246,992 B1 | 6/2001 | Brown |
| 6,259,937 B1 | 7/2001 | Schulman et al. |
| 6,329,161 B1 | 12/2001 | Heller et al. |
| 6,408,330 B1 | 6/2002 | DeLaHuerga |
| 6,424,847 B1 | 7/2002 | Mastrototaro et al. |
| 6,472,122 B1 | 10/2002 | Schulman et al. |
| 6,484,045 B1 | 11/2002 | Holker et al. |

(56) References Cited

U.S. PATENT DOCUMENTS

| | | |
|---|---|---|
| 6,484,046 B1 | 11/2002 | Say et al. |
| 6,503,381 B1 | 1/2003 | Gotoh et al. |
| 6,514,718 B2 | 2/2003 | Heller et al. |
| 6,544,173 B2 | 4/2003 | West et al. |
| 6,553,263 B1 | 4/2003 | Meadows et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,641,533 B2 | 11/2003 | Causey, III et al. |
| 6,654,625 B1 | 11/2003 | Say et al. |
| 6,659,980 B2 | 12/2003 | Moberg et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,728,576 B2 | 4/2004 | Thompson et al. |
| 6,733,471 B1 | 5/2004 | Ericson et al. |
| 6,746,582 B2 | 6/2004 | Heller et al. |
| 6,747,556 B2 | 6/2004 | Medema et al. |
| 6,749,740 B2 | 6/2004 | Liamos et al. |
| 6,752,787 B1 | 6/2004 | Causey, III et al. |
| 6,809,653 B1 | 10/2004 | Mann et al. |
| 6,881,551 B2 | 4/2005 | Heller et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,916,159 B2 | 7/2005 | Rush et al. |
| 6,932,584 B2 | 8/2005 | Gray et al. |
| 6,932,894 B2 | 8/2005 | Mao et al. |
| 6,942,518 B2 | 9/2005 | Liamos et al. |
| 7,153,263 B2 | 12/2006 | Carter et al. |
| 7,153,289 B2 | 12/2006 | Vasko |
| 7,396,330 B2 | 7/2008 | Banet et al. |
| 2001/0044731 A1 | 11/2001 | Coffman et al. |
| 2002/0013518 A1 | 1/2002 | West et al. |
| 2002/0055857 A1 | 5/2002 | Mault et al. |
| 2002/0082665 A1 | 6/2002 | Haller et al. |
| 2002/0137997 A1 | 9/2002 | Mastrototaro et al. |
| 2002/0161288 A1 | 10/2002 | Shin et al. |
| 2003/0060765 A1 | 3/2003 | Campbell et al. |
| 2003/0078560 A1 | 4/2003 | Miller et al. |
| 2003/0088166 A1 | 5/2003 | Say et al. |
| 2003/0144581 A1 | 7/2003 | Conn et al. |
| 2003/0152823 A1 | 8/2003 | Heller |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0208113 A1 | 11/2003 | Mault et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0073095 A1 | 4/2004 | Causey, III et al. |
| 2004/0074785 A1 | 4/2004 | Holker et al. |
| 2004/0093167 A1 | 5/2004 | Braig et al. |
| 2004/0097796 A1 | 5/2004 | Berman et al. |
| 2004/0102683 A1 | 5/2004 | Khanuja et al. |
| 2004/0111017 A1 | 6/2004 | Say et al. |
| 2004/0122353 A1 | 6/2004 | Shahmirian et al. |
| 2004/0167465 A1 | 8/2004 | Mihai et al. |
| 2004/0263354 A1 | 12/2004 | Mann et al. |
| 2005/0038331 A1 | 2/2005 | Silaski et al. |
| 2005/0038680 A1 | 2/2005 | McMahon et al. |
| 2005/0154271 A1 | 7/2005 | Rasdal et al. |
| 2005/0192557 A1 | 9/2005 | Brauker et al. |
| 2006/0229694 A1 | 10/2006 | Schulman et al. |
| 2006/0238333 A1 | 10/2006 | Welch et al. |
| 2006/0293571 A1 | 12/2006 | Bao et al. |
| 2007/0088521 A1 | 4/2007 | Shmueli et al. |
| 2007/0135866 A1 | 6/2007 | Baker et al. |
| 2007/0227912 A1* | 10/2007 | Chatelier ............ A61B 5/1486 205/792 |
| 2008/0154503 A1 | 6/2008 | Wittenber et al. |
| 2008/0197024 A1* | 8/2008 | Simpson ............ A61B 5/14542 205/778 |
| 2009/0081951 A1 | 3/2009 | Erdmann et al. |
| 2009/0082635 A1 | 3/2009 | Baldus et al. |
| 2009/0131768 A1* | 5/2009 | Simpson ............ A61B 5/0031 600/309 |
| 2012/0097554 A1* | 4/2012 | Shah ................ G01N 27/3274 205/782 |
| 2012/0186997 A1* | 7/2012 | Li .......................... C12Q 1/00 205/778 |
| 2013/0075277 A1* | 3/2013 | Kaneda ................ C12Q 1/004 205/777.5 |
| 2013/0328572 A1* | 12/2013 | Wang .................... G01R 35/00 324/601 |
| 2014/0046149 A1* | 2/2014 | Simpson ............ A61B 5/14532 600/316 |

FOREIGN PATENT DOCUMENTS

| | | |
|---|---|---|
| EP | 0806738 | 11/1997 |
| EP | 0880936 | 12/1998 |
| EP | 1338295 | 8/2003 |
| EP | 1631036 A2 | 3/2006 |
| GB | 2218831 | 11/1989 |
| WO | WO 96/20745 | 7/1996 |
| WO | WO 96/36389 | 11/1996 |
| WO | WO 96/37246 A1 | 11/1996 |
| WO | WO 97/21456 | 6/1997 |
| WO | WO 98/20439 | 5/1998 |
| WO | WO 98/24358 | 6/1998 |
| WO | WO 98/42407 | 10/1998 |
| WO | WO 98/49659 | 11/1998 |
| WO | WO 98/59487 | 12/1998 |
| WO | WO 99/08183 | 2/1999 |
| WO | WO 99/10801 | 3/1999 |
| WO | WO 99/18532 | 4/1999 |
| WO | WO 99/22236 | 5/1999 |
| WO | WO 00/10628 | 3/2000 |
| WO | WO 00/19887 | 4/2000 |
| WO | WO 00/48112 | 8/2000 |
| WO | WO 02/058537 A2 | 8/2002 |
| WO | WO 03/001329 | 1/2003 |
| WO | WO 03/094090 | 11/2003 |
| WO | WO 2005/065538 A2 | 7/2005 |
| WO | WO 2013/184416 A2 | 12/2013 |

OTHER PUBLICATIONS

PCT Search Report (PCT/US02/03299), dated Oct. 31, 2001, Medtronic Minimed, Inc.

(Animas Corporation, 1999). Animas . . . bringing new life to insulin therapy.

Bode B W, et al. (1996). Reduction in Severe Hypoglycemia with Long-Term Continuous Subcutaneous Insulin Infusion in Type I Diabetes. Diabetes Care, vol. 19, No. 4, 324-327.

Boland E (1998). Teens Pumping it Up! Insulin Pump Therapy Guide for Adolescents. 2nd Edition.

Brackenridge B P (1992). Carbohydrate Gram Counting A Key to Accurate Mealtime Boluses in Intensive Diabetes Therapy. Practical Diabetology, vol. 11, No. 2, pp. 22-28.

Brackenridge, B P et al. (1995). Counting Carbohydrates How to Zero in on Good Control. MiniMed Technologies Inc.

Farkas-Hirsch R et al. (1994). Continuous Subcutaneous Insulin Infusion: A Review of the Past and Its Implementation for the Future. Diabetes Spectrum From Research to Practice, vol. 7, No. 2, pp. 80-84, 136-138.

(56) References Cited

OTHER PUBLICATIONS

Hirsch I B et al. (1990). Intensive Insulin Therapy for Treatment of Type I Diabetes. Diabetes Care, vol. 13, No. 12, pp. 1265-1283.
Kulkarni K et al. (1999). Carbohydrate Counting A Primer for Insulin Pump Users to Zero in on Good Control. MiniMed Inc.
Marcus A O et al. (1996). Insulin Pump Therapy Acceptable Alternative to Injection Therapy. Postgraduate Medicine, vol. 99, No. 3, pp. 125-142.
Reed J et al. (1996). Voice of the Diabetic, vol. 11, No. 3, pp. 1-38.
Skyler J S (1989). Continuous Subcutaneous Insulin Infusion [CSII] With External Devices: Current Status. Update in Drug Delivery Systems, Chapter 13, pp. 163-183. Futura Publishing Company.
Skyler J S et al. (1995). The Insulin Pump Therapy Book Insights from the Experts. MiniMed•Technologies.
Strowig S M (1993). Initiation and Management of Insulin Pump Therapy. The Diabetes Educator, vol. 19, No. 1, pp. 50-60.
Walsh J, et al. (1989). Pumping Insulin: The Art of Using an Insulin Pump. Published by MiniMed•Technologies.
(Intensive Diabetes Management, 1995). insulin Infusion Pump Therapy. pp. 66-78.
Disetronic My Choice™ D-TRON™ Insulin Pump Reference Manual. (no date).
Disetronic H-TRON® plus Quick Start Manual. (no date).
Disetronic My Choice H-TRONplus Insulin Pump Reference Manual. (no date).
Disetronic H-TRON®plus Reference Manual. (no date).
(MiniMed, 1996). The MiniMed 506. 7 pages. Retrieved on Sep. 16, 2003 from the World Wide Web: http://web.archive.org/web/19961111054527/www.minimed.com/files/506_pic.htm.
(MiniMed, 1997). MiniMed 507 Specifications. 2 pages. Retrieved on Sep. 16, 2003 from the World Wide Web: http://web.archive.org/web/19970124234841/www.minimed.com/files/mmn075.htm.
(MiniMed, 1996). FAQ: The Practical Things . . . pp. 1-4. Retrieved on Sep. 16, 2003 from the World Wide Web: http://web.archive.org/web/19961111054546/www.minimed.com/files/faq_pract.htm.
(MiniMed, 1997). Wanted: a Few Good Belt Clips! 1 page. Retrieved on Sep. 16, 2003 from the World Wide Web: http://web.archive.org/web/19970124234559/www.minimed.com/files/mmn002.htm.
(MiniMed Technologies, 1994). MiniMed 506 Insulin Pump User's Guide.
(MiniMed Technologies, 1994). MiniMed™ Dosage Calculator Initial Meal Bolus Guidelines / MiniMed™ Dosage Calculator Initial Basal Rate Guidelines Percentage Method. 4 pages.
(MiniMed, 1996). MiniMed™ 507 Insulin Pump User's Guide.
(MiniMed, 1997). MiniMed™ 507 Insulin Pump User's Guide.
(MiniMed, 1998). MiniMed 507C Insulin Pump User's Guide.
(MiniMed International, 1998). MiniMed 507C Insulin Pump for those who appreciate the difference.
(MiniMed Inc., 1999). MiniMed 508 Flipchart Guide to Insulin Pump Therapy.
(MiniMed Inc., 1999). Insulin Pump Comparison / Pump Therapy Will Change Your Life.
(MiniMed, 2000). MiniMed® 508 User's Guide.
(MiniMed Inc., 2000). MiniMed® Now [I] Can Meal Bolus Calculator / MiniMed® Now [I] Can Correction Bolus Calculator.
(MiniMed Inc., 2000). Now [I] Can MiniMed Pump Therapy.
(MiniMed Inc., 2000). Now [I] Can MiniMed Diabetes Management.
(Medtronic MiniMed, 2002). The 508 Insulin Pump A Tradition of Excellence.
(Medtronic MiniMed, 2002). Medtronic MiniMed Meal Bolus Calculator and Correction Bolus Calculator. International Version.
Abel, P., et al., "Experience with an implantable glucose sensor as a prerequiste of an artificial beta cell," Biomed. Biochim. Acta 43 (1984) 5, pp. 577-584.
Bindra, Dilbir S., et al., "Design and in Vitro Studies of a Needle-Type Glucose Sensor for a Subcutaneous Monitoring," American Chemistry Society, 1991, 63, pp. 1692-1696.
Boguslavsky, Leonid, et al., "Applications of redox polymers in biosensors," Sold State Ionics 60, 1993, pp. 189-197.

Geise, Robert J., et al., "Electropolymerized 1,3-diaminobenzene for the construction of a 1,1'-dimethylferrocene mediated glucose biosensor," Analytica Chimica Acta, 281, 1993, pp. 467-473.
Gernet, S., et al., "A Planar Glucose Enzyme Electrode," Sensors and Actuators, 17, 1989, pp. 537-540.
Gernet, S., et al., "Fabrication and Characterization of a Planar Electromechanical Cell and its Application as a Glucose Sensor," Sensors and Actuators, 18, 1989, pp. 59-70.
Gorton, L., et al., "Amperometric Biosensors Based on an Apparent Direct Electron Transfer Between Electrodes and Immobilized Peroxiases," Analyst, Aug. 1991, vol. 117, pp. 1235-1241.
Gorton, L., et al., "Amperometric Glucose Sensors Based on Immobilized Glucose-Oxidizing Enymes and Chemically Modified Electrodes," Analytica Chimica Acta, 249, 1991, pp. 43-54.
Gough, D. A., et al., "Two-Dimensional Enzyme Electrode Sensor for Glucose," Analytical Chemistry, vol. 57, No. 5, 1985, pp. 2351-2357.
Gregg, Brian A., et al., "Cross-Linked Redox Gels Containing Glucose Oxidase for Amperometric Biosensor Applications," Analytical Chemistry, 62, pp. 258-263.
Gregg, Brian A., et al., "Redox Polymer Films Containing Enzymes. 1. A Redox-Conducting Epoxy Cement: Synthesis, Characterization, and Electrocatalytic Oxidation of Hydroquinone," The Journal of Physical Chemistry, vol. 95, No. 15, 1991, pp. 5970-5975.
Hashiguchi, Yasuhiro, MD, et al., "Development of a Miniaturized Glucose Monitoring System by Combining a Needle-Type Glucose Sensor With Microdialysis Sampling Method," Diabetes Care, vol. 17, No. 5, May 1994, pp. 387-389.
Heller, Adam, "Electrical Wiring of Redox Enzymes," Acc. Chem. Res., vol. 23, No. 5, May 1990, pp. 128-134.
Jobst, Gerhard, et al., "Thin-Film Microbiosensors for Glucose-Lactate Monitoring," Analytical Chemistry, vol. 68, No. 18, Sep. 15, 1996, pp. 3173-3179.
Johnson, K.W., et al., "In vivo evaluation of an electroenzymatic glucose sensor implanted in subcutaneous tissue," Biosensors & Bioelectronics, 7, 1992, pp. 709-714.
Jönsson, G., et al., "An Electromechanical Sensor for Hydrogen Peroxide Based on Peroxidase Adsorbed on a Spectrographic Graphite Electrode," Electroanalysis, 1989, pp. 465-468.
Kanapieniene, J. J., et al., "Miniature Glucose Biosensor with Extended Linearity," Sensors and Actuators, B. 10, 1992, pp. 37-40.
Kawamori, Ryuzo, et al., "Perfect Normalization of Excessive Glucagon Responses to Intraveneous Arginine in Human Diabetes Mellitus With the Artificial Beta-Cell," Diabetes vol. 29, Sep. 1980, pp. 762-765.
Kimura, J., et al., "An Immobilized Enzyme Membrane Fabrication Method," Biosensors 4, 1988, pp. 41-52.
Koudelka, M., et al., "In-vivo Behaviour of Hypodermically Implanted Microfabricated Glucose Sensors," Biosensors & Bioelectronics 6, 1991, pp. 31-36.
Koudelka, M., et al., "Planar Amperometric Enzyme-Based Glucose Microelectrode," Sensors & Actuators, 18, 1989, pp. 157-165.
Mastrototaro, John J., et al., "An electroenzymatic glucose sensor fabricated on a flexible substrate," Sensors & Actuators, B. 5, 1991, pp. 139-144.
Mastrototaro, John J., et al., "An Electroenzymatic Sensor Capable of 72 Hour Continuous Monitoring of Subcutaneous Glucose," 14th Annual International Diabetes Federation Congress, Washington D.C., Jun. 23-28, 1991.
McKean, Brian D., et al., "A Telemetry-Instrumentation System for Chronically Implanted Glucose and Oxygen Sensors," IEEE Transactions on Biomedical Engineering, Vo. 35, No. 7, Jul. 1988, pp. 526-532.
Monroe, D., "Novel Implantable Glucose Sensors," ACL, Dec. 1989, pp. 8-16.
Morff, Robert J., et al., "Microfabrication of Reproducible, Economical, Electroenzymatic Glucose Sensors," Annuaal International Conference of teh IEEE Engineering in Medicine and Biology Society, Vo. 12, No. 2, 1990, pp. 483-484.
Moussy, Francis, et al., "Performance of Subcutaneously Implanted Needle-Type Glucose Sensors Employing a Novel Trilayer Coating," Analytical Chemistry, vol. 65, No. 15, Aug. 1, 1993, pp. 2072-2077.

(56) References Cited

OTHER PUBLICATIONS

Nakamoto, S., et al., "A Lift-Off Method for Patterning Enzyme-Immobilized Membranes in Multi-Biosensors," Sensors and Actuators 13, 1988, pp. 165-172.

Nishida, Kenro, et al., "Clinical applications of teh wearable artificial endocrine pancreas with the newly designed needle-type glucose sensor," Elsevier Sciences B.V., 1994, pp. 353-358.

Nishida, Kenro, et al., "Development of a ferrocene-mediated needle-type glucose sensor covereed with newly designd biocompatible membrane, 2-methacryloyloxyethylphosphorylcholine -co-n-butyl nethacrylate," Medical Progress Through Technology, vol. 21, 1995, pp. 91-103.

Poitout, V., et al., "A glucose monitoring system for on line estimation oin man of blood glucose concentration using a miniaturized glucose sensor implanted in the subcutaneous tissue adn a wearable control unit," Diabetologia, vol. 36, 1991, pp. 658-663.

Reach, G., "A Method for Evaluating in vivo the Functional Characteristics of Glucose Sensors," Biosensors 2, 1986, pp. 211-220.

Shaw, G. W., et al., "In vitro testing of a simply constructed, highly stable glucose sensor suitable for implantation in diabetic patients," Biosensors & Bioelectronics 6, 1991, pp. 401-406.

Shichiri, M., "A Needle-Type Glucose Sensor—A Valuable Tool Not Only for a Self-Blood Glucose Monitoring but for a Wearable Artifiical Pancreas," Life Support Systems Proceedings, XI Annual Meeting ESAO, Alpbach-Innsbruck, Austria, Sep. 1984, pp. 7-9.

Shichiri, Motoaki, et al., "An artificial endocrine pancreas—problems awaiting solution for long-term clinical applications of a glucose sensor," Frontiers Med. Biol. Engng., 1991, vol. 3, No. 4, pp. 283-292.

Shichiri, Motoaki, et al., "Closed-Loop Glycemic Control with a Wearable Artificial Endocrine Pancreas—Variations in Daily Insulin Requirements to Glycemic Response," Diabetes, vol. 33, Dec. 1984, pp. 1200-1202.

Shichiri, Motoaki, et al., "Glycaemic Control in a Pacreatectomized Dogs with a Wearable Artificial Endocrine Pancreas," Diabetologia, vol. 24, 1983, pp. 179-184.

Shichiri, M., et al., "In Vivo Characteristics of Needle-Type Glucose Sensor—Measurements of Subcutaneous Glucose Concentrations in Human Volunteers," Hormone and Metabolic Research, Supplement Series vol. No. 20, 1988, pp. 17-20.

Shichiri, M., et al., "Membrane design for extending the long-life of an implantable glucose sensor," Diab. Nutr. Metab., vol. 2, No. 4, 1989, pp. 309-313.

Shichiri, Motoaki, et al., "Normalization of the Paradoxic Secretion of Glucagon in Diabetes Who Were Controlled by the Artificial Beta Cell," Diabetes, vol. 28, Apr. 1979, pp. 272-275.

Shichiri, Motoaki, et al., "Telemetry Glucose Monitoring Device with Needle-Type Glucose Sensor: A useful Tool for Blood Glucose Monitoring in Diabetic Individuals," Diabetes Care, vol. 9, No. 3, May-Jun. 1986, pp. 298-301.

Shichiri, Motoaki, et al., "Wearable Artificial Endocrine Pancreas with Needle-Type Glucose Sensor," The Lancet, Nov. 20, 1982, pp. 1129-1131.

Shichiri, Motoaki, et al., "The Wearable Artificial Endocrine Pancreas with a Needle-Type Glucose Sensor: Perfect Glycemic Control in Ambulatory Diabetes," Acta Paediatr Jpn 1984, vol. 26, pp. 359-370.

Shinkai, Seiji, "Molecular Recognition of Mono- and Di-saccharides by Phenylboronic Acids in Solvent Extraction and as a Monolayer," J. Chem. Soc., Chem. Commun., 1991, pp. 1039-1041.

Shults, Mark C., "A Telemetry-Instrumentation System for Monitoring Multiple Subcutaneously Implanted Glucose Sensors," IEEE Transactions on Biomedical Engineering, vol. 41, No. 10, Oct. 1994, pp. 937-942.

Sternberg, Robert, et al., "Study and Development of Multilayer Needle-type Enzyme-based Glucose Microsensors," Biosensors, vol. 4, 1988, pp. 27-40.

Tamiya, E., et al., "Micro Glucose Sensors using Electron Mediators Immobilized on a Polypyrrole-Modified Electrode," Sensors and Actuators, vol. 18, 1989, pp. 297-307.

Tsukagoshi, Kazuhiko, et al., "Specific Complexation with Mono- and Disaccharides that can be Detected by Circular Dichroism," J. Org. Chem., vol. 56, 1991, pp. 4089-4091.

Urban, G., et al., "Miniaturized multi-enzyme biosensors integrated with pH sensors on flexible polymer carriers for in vivo applciations," Biosensors & Bioelectronics, vol. 7, 1992, pp. 733-739.

Ubran, G., et al., "Miniaturized thin-film biosensors using covalently immobilized glucose oxidase," Biosensors & Bioelectronics, vol. 6, 1991, pp. 555-562.

Velho, G., et al., "In vivo calibration of a subcutaneous glucose sensor for determination of subcutaneous glucose kinetics," Diab. Nutr. Metab., vol. 3, 1988, pp. 227-233.

Wang, Joseph, et al., "Needle-Type Dual Microsensor for the Simultaneous Monitoring of Glucose and Insulin," Analytical Chemistry, vol. 73, 2001, pp. 844-847.

Yamasaki, Yoshimitsu, et al., "Direct Measurement of Whole Blood Glucose by a Needle-Type Sensor," Clinics Chimica Acta, vol. 93, 1989, pp. 93-98.

Yokoyama, K., "Integrated Biosensor for Glucose and Galactose," Analytica Chimica Acta, vol. 218, 1989, pp. 137-142.

\* cited by examiner

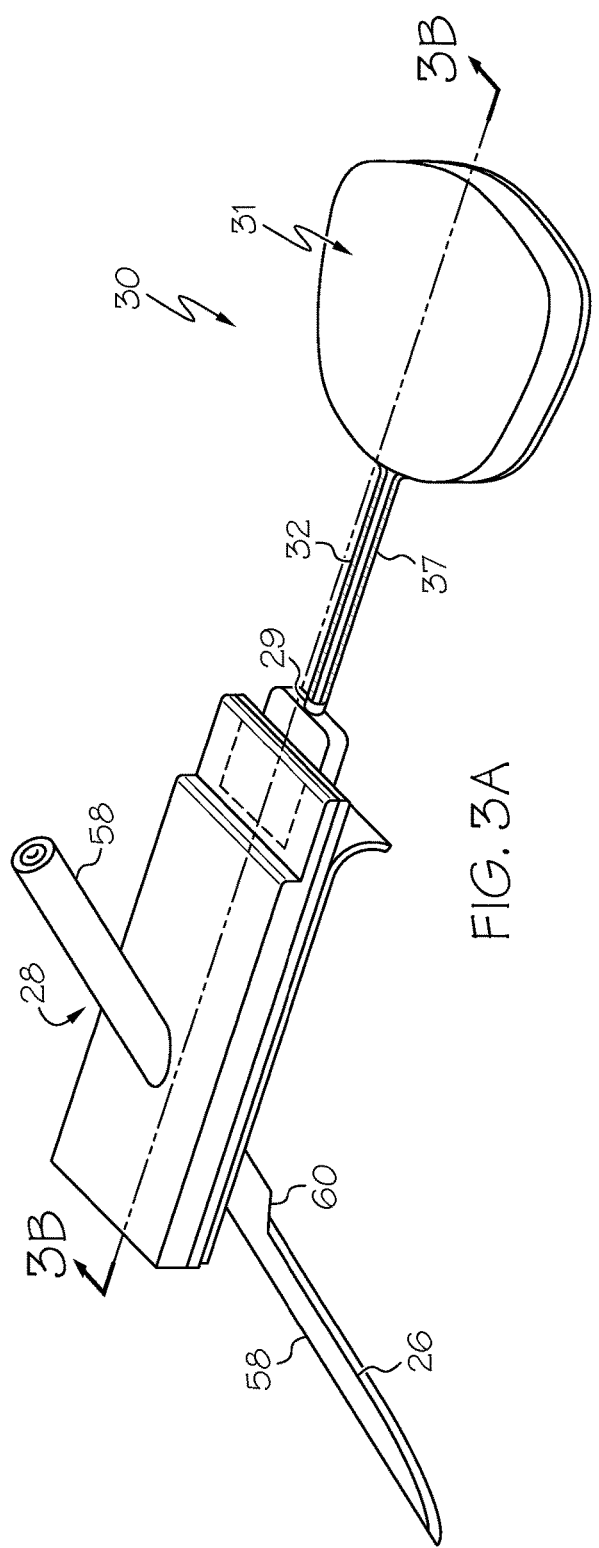
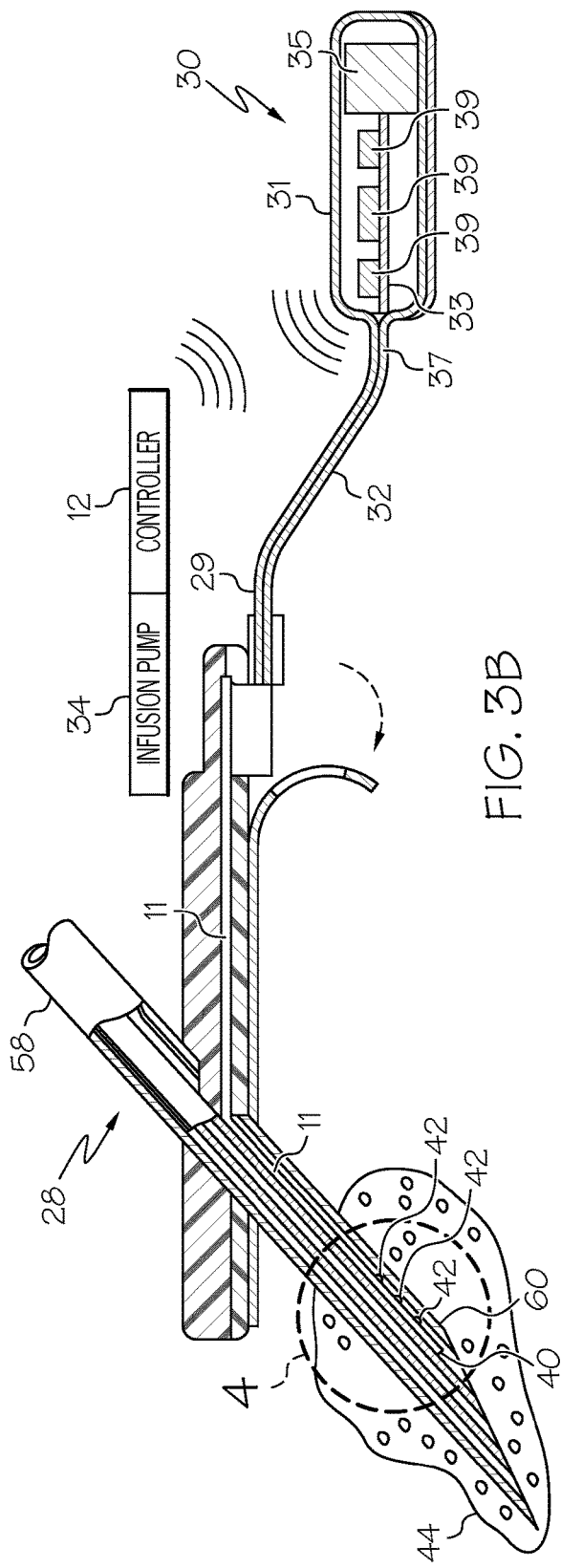
FIG. 3A
FIG. 3B

METHOD FOR MONITORING AN ANALYTE, ANALYTE SENSOR AND ANALYTE MONITORING APPARATUS

TECHNICAL FIELD

Embodiments of the subject matter described herein relate generally to monitoring analyte levels in patients. More particularly, embodiments of the subject matter relate to glucose sensors.

BACKGROUND

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Currently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

An infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded analyte sensor, such as a glucose sensor, in real-time.

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

Equation 1

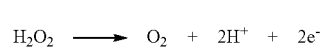

Equation 2

In equation 1, the glucose oxidase is used to catalyze the reaction between glucose and oxygen to yield gluconic acid and hydrogen peroxide ($H_2O_2$). The hydrogen peroxide reacts electrochemically as shown in equation 2 and the resulting current can be measured by a potentiostat. These reactions, which occur in a variety of oxidoreductases known in the art, are used in a number of sensor designs.

As analyte sensor technology matures and new applications for sensor technology are developed, there is a need for improved methods for monitoring analyte levels in patients that facilitate the use of sensors in the wide variety of situations in which the measurement of an analyte is desirable.

Accordingly, it is desirable to have an improved analyte sensor and related monitoring apparatus and method that address the shortcomings of traditional sensor systems. Furthermore, other desirable features and characteristics will become apparent from the subsequent detailed description and the appended claims, taken in conjunction with the accompanying drawings and the foregoing technical field and background.

BRIEF SUMMARY

A method for monitoring an analyte within the body of a patient is provided here. In accordance with certain embodiments, the method for monitoring an analyte within the body of a patient includes implanting an analyte sensor at a sensor placement site in the patient. The analyte sensor includes a reference electrode, a counter electrode, a primary working electrode having a first structure, and an auxiliary working electrode having a second structure different from the first structure. The method includes communicating a primary signal from the primary working electrode and an auxiliary signal from the auxiliary working electrode to a processor. Further, the method includes monitoring the primary signal and the auxiliary signal with the processor to characterize a change in a physiological characteristic at the sensor placement site.

An exemplary embodiment of an analyte sensor system is also presented here. The analyte sensor includes a reference electrode, a counter electrode, a primary working electrode, and an auxiliary working electrode. The primary working electrode has a first structure and the auxiliary working electrode has a second structure different from the first structure.

Also provided is an exemplary embodiment of an analyte monitoring apparatus. The analyte monitoring apparatus includes a base element adapted to secure the apparatus to the patient. The analyte monitoring apparatus also includes a piercing member coupled to and extending from the base element. Further, the analyte monitoring apparatus includes an electrochemical sensor for monitoring an electrochemical sensor placement site. The electrochemical sensor is operatively coupled to the piercing member and includes a reference electrode, a counter electrode, a primary working electrode having a first structure, and an auxiliary working electrode having a second structure different from the first structure. The analyte monitoring apparatus also includes a sensor input capable of receiving signals from the electrochemical sensor and a processor coupled to the sensor input.

The processor is capable of characterizing one or more signals received from the electrodes of the electrochemical sensor.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIG. 3A is a perspective view of an analyte monitoring apparatus for use in accordance with an embodiment.

FIG. 3B is a side cross-sectional view of the analyte monitoring apparatus of FIG. 3A for an embodiment.

DETAILED DESCRIPTION

Figure 1:
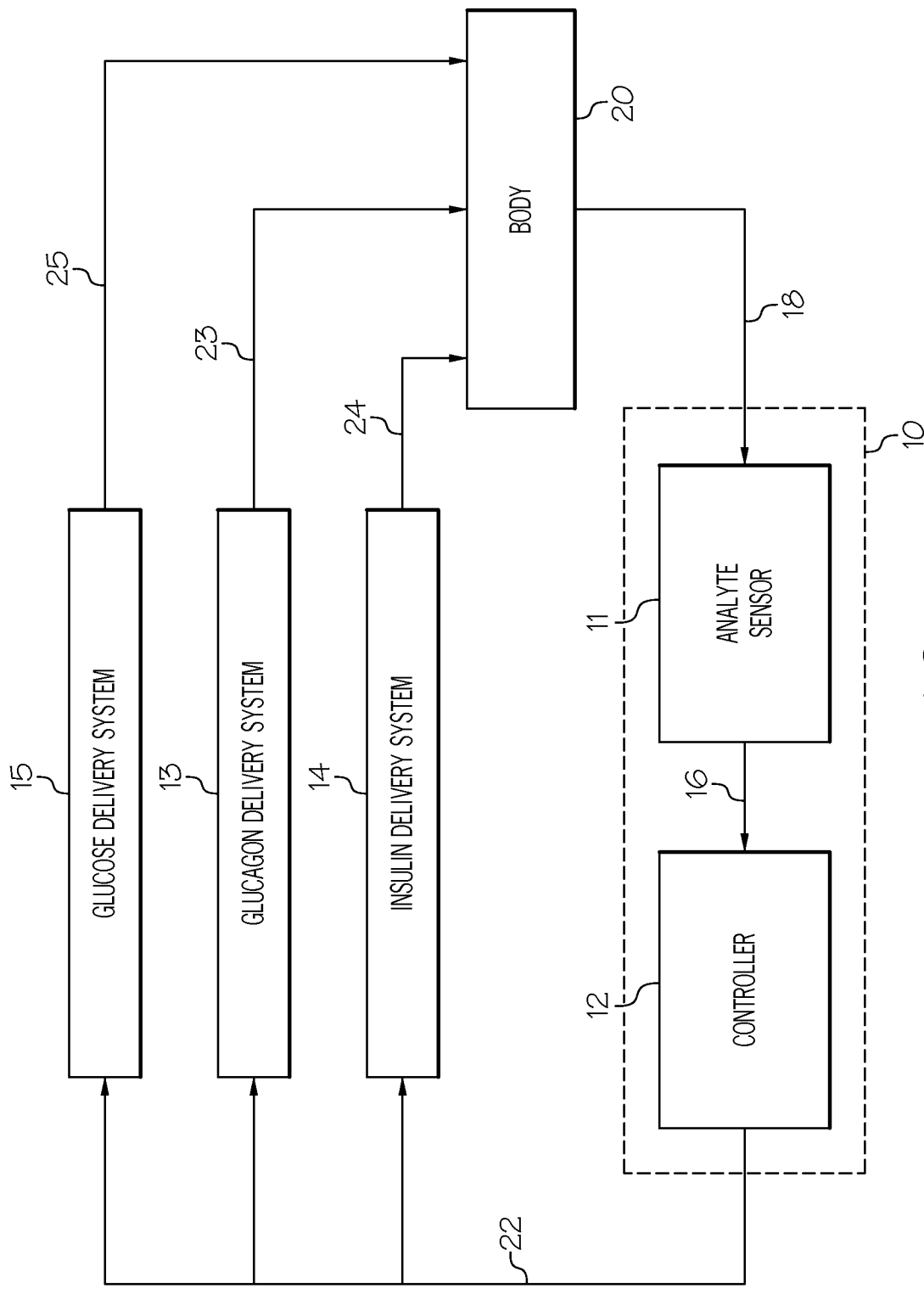
FIG. 1 is a block diagram of an analyte monitoring apparatus in accordance with an embodiment.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description. Also, while the preceding background discusses glucose sensing and exemplary analyte sensors are described as glucose sensors herein, such description is for convenience and is not limiting. The claimed subject matter may include any type of analyte sensor utilizing an embodiment of the sensor electrodes described herein.

In an exemplary analyte monitoring apparatus, blood-glucose measurements may be employed in a closed loop infusion system for regulating a rate of fluid infusion into a body. In particular embodiments, a control system may be adapted to regulate a rate of insulin, glucagon, and/or glucose infusion into a body of a patient based, at least in part, on a glucose concentration measurement taken from a body (e.g., from a glucose sensor).

According to certain embodiments, examples of analyte sensors and/or monitoring apparatuses as described herein may be implemented in a hospital environment to monitor levels of glucose in a patient. Alternatively, according to certain embodiments, examples of analyte sensors and/or monitoring apparatuses as described herein may be implemented in non-hospital environments to monitor levels of glucose in a patient. Here, a patient or other non-medical professional may be responsible for interacting with an analyte sensors and/or monitoring apparatuses.

To maintain healthy glucose levels, a person with type 1 diabetes may manage their glycemia by monitoring blood glucose levels, controlling diet, exercise, and self-administering appropriate amounts of insulin at appropriate times. Deviations from such glycemic management, such as skipping an insulin bolus at meal time or underestimating the carbohydrate content of a meal may bring about prolonged hyperglycemia. Likewise, receiving too much insulin (e.g., by over-bolusing) for a given blood glucose level and/or meal may bring about severe hypoglycemia. Other external factors, such as exercise or stress, may also contribute to glycemic deviations.

Errors in reading glucose levels may contribute to providing too much or too little insulin. For example, low oxygen (local hypoxia) and/or the presence of an electroactive interferent in vivo at the monitoring site may cause gradual or incisive transgression toward an unsuitable glucose sensing environment. As a result, issues like current dips, sensor sensitivity loss, and false sensor glucose overreading (increased current in response to the presence of an electroactive interferent) may occur.

A particular embodiment of an analyte sensor or monitoring apparatus has the diagnostic capability to detect or characterize changes in glucose to oxygen molar ratios in vivo (e.g., reduction in local subcutaneous oxygen). Another particular embodiment of an analyte sensor or monitoring apparatus has the diagnostic capability to detect or characterize transient incisive but false increase in sensor glucose value due to introduction of electroactive interferents. Such embodiments may reduce the risk of hypoglycemia and hyperglycemia by eliminating or reducing analyte monitoring error.

By more accurately monitoring a patient's glucose level and maintaining appropriate infusion rates, extreme glycemic variations may be reduced or avoided altogether. This may provide a patient with improved glycemic control in circumstances in which they would otherwise be exposed to undesirable extremes of glycemia.

FIG. 1 is a block diagram of an example analyte monitoring apparatus 10 for use with a glucose control system in accordance with an embodiment. Particular embodiments of the analyte monitoring apparatus 10 may include an analyte sensor 11 and a controller 12. The analyte monitoring apparatus 10 is provided for use with an insulin delivery system 14, a glucagon delivery system 13, and a glucose delivery system 15, as shown in FIG. 1. The analyte monitoring apparatus 10 may be considered to include the insulin delivery system 14, glucagon delivery system 13, and glucose delivery system 15.

In certain exemplary embodiments, analyte sensor 11 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and provide glucose 25 into body 20 in response to commands 22.

Analyte sensor 11 may include a glucose sensor, sensor electrical components to provide power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using, e.g., a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor. It should be understood, however that using a blood glucose sensor is only one particular technique for obtaining such observations or measurements, and that other techniques, such as measuring blood glucose inform observations of other body fluids (e.g., observations of the presence of glucose in interstitial fluid using a subcutaneous sensor), may be used without deviating from claimed subject matter.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) including a data input device and/or a data output device. Such a data output device may, for example, generate signals to initiate an alarm and/or include a display or printer for showing status of a controller 12 and/or a patient's vital indicators. Such a data input device may include dials, buttons, pointing devices, manual switches, alphanumeric keys, a touch-sensitive display, combinations thereof, and/or the like for receiving user and/or operator inputs. Such a data input device may be used for scheduling and/or initiating insulin bolus injections for meals, for example. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular embodiments, controller 12 may be housed in an infusion device housing, and an infusion communication system may include an electrical trace or a wire that carries commands 22 from controller 12 to an infusion device. In alternative embodiments, controller 12 may be housed in a sensor system housing, and a sensor communication system may include an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable, a wire, a fiber optic line, RF, IR, or ultrasonic transmitters and receivers, combinations thereof, and/or the like instead of electrical traces, just to name a few examples.

Figure 2:
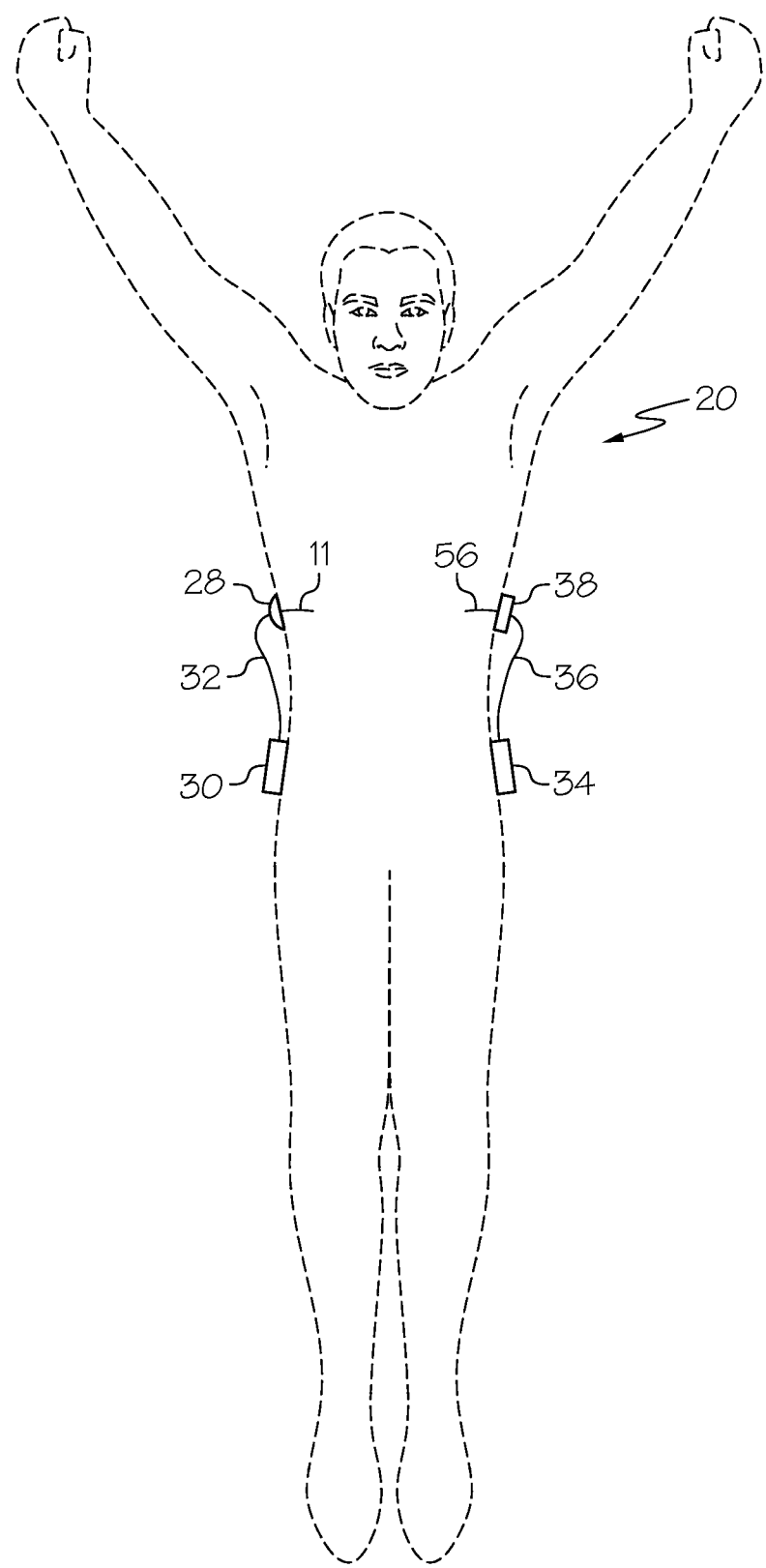
FIG. 2 is a front view of an analyte monitoring apparatus located on a body in accordance with an embodiment.
Figure 3C:
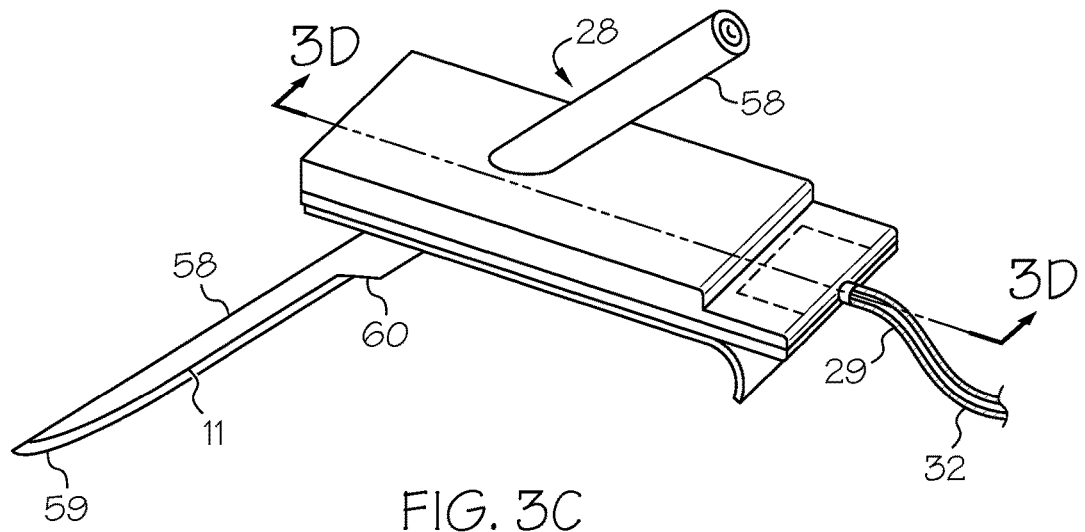
FIG. 3C is a perspective view of the analyte monitoring apparatus of FIG. 3A for an embodiment.
Figure 3D:
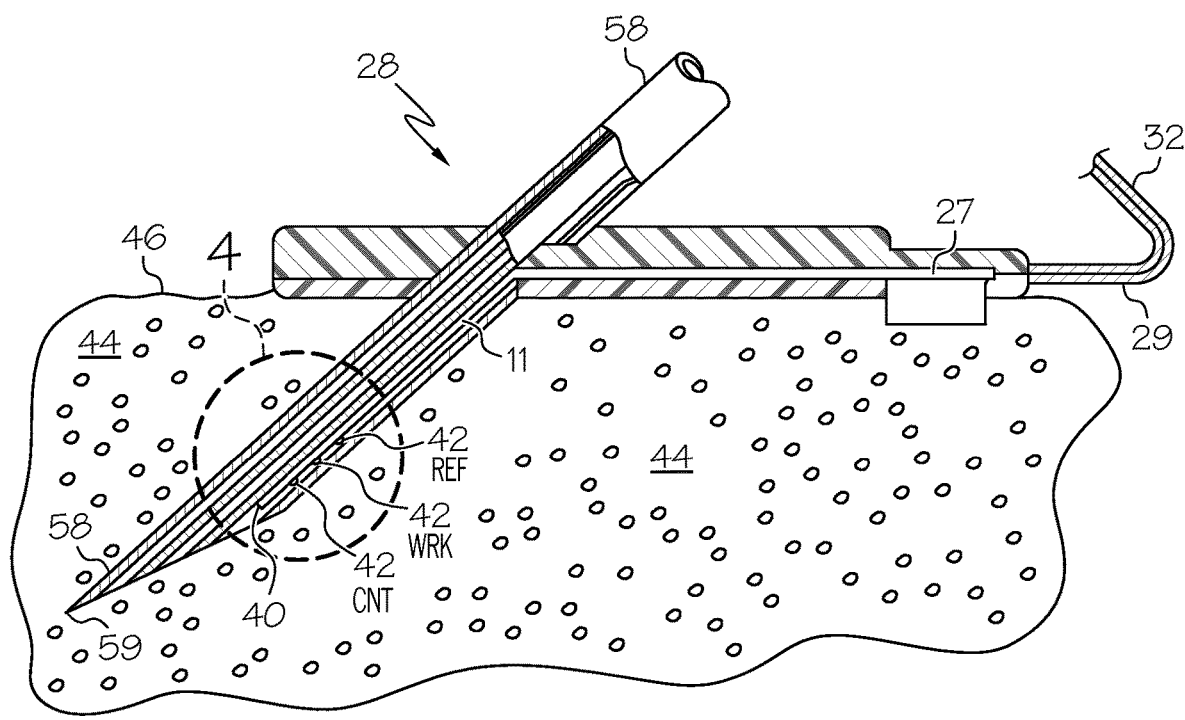
FIG. 3D is a side cross-sectional view of the analyte monitoring apparatus of FIG. 3C for an embodiment.
Figure 4:
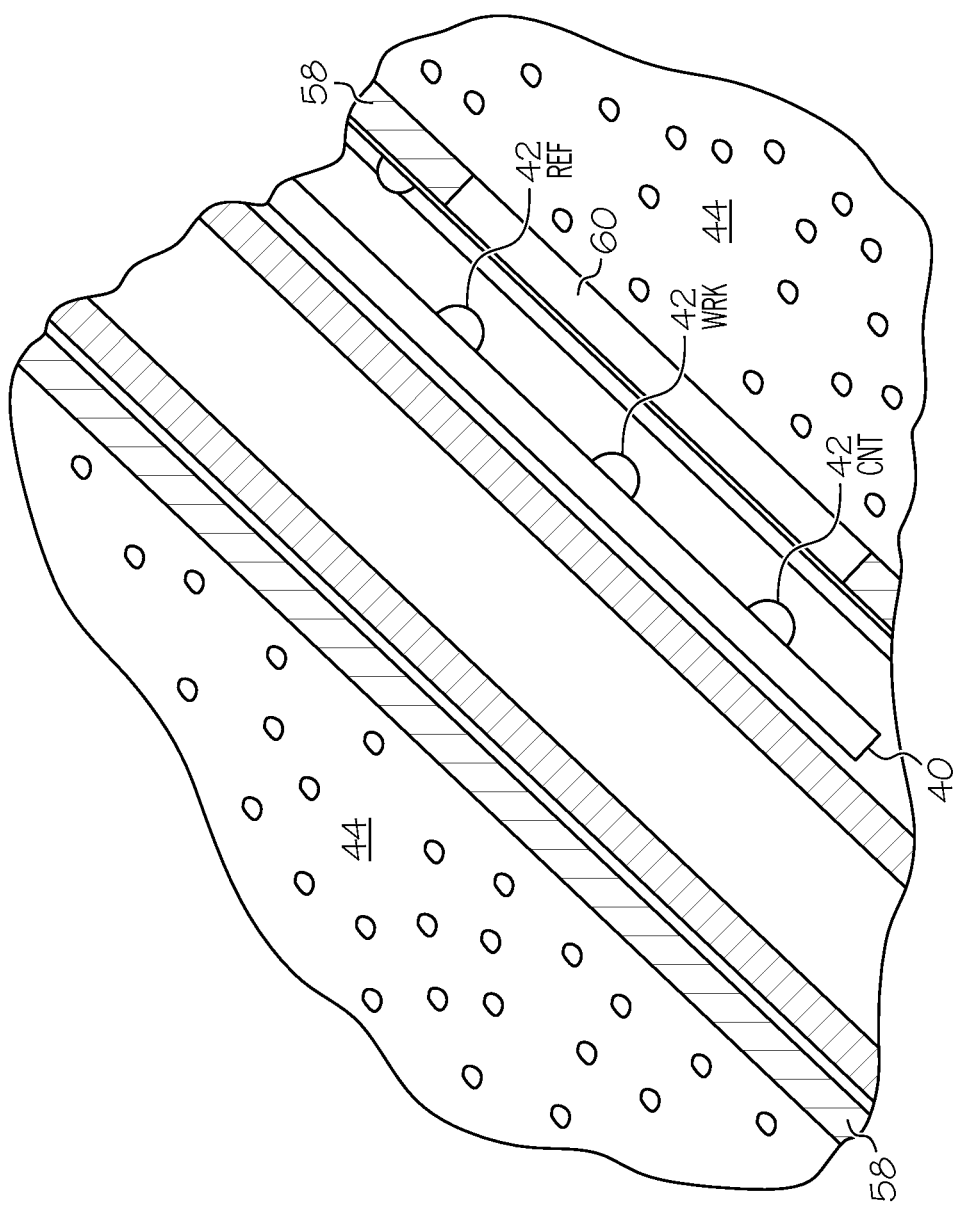
FIG. 4 is a cross sectional view of a sensing end of an analyte sensor of FIG. 3D for an embodiment.
Figure 5:
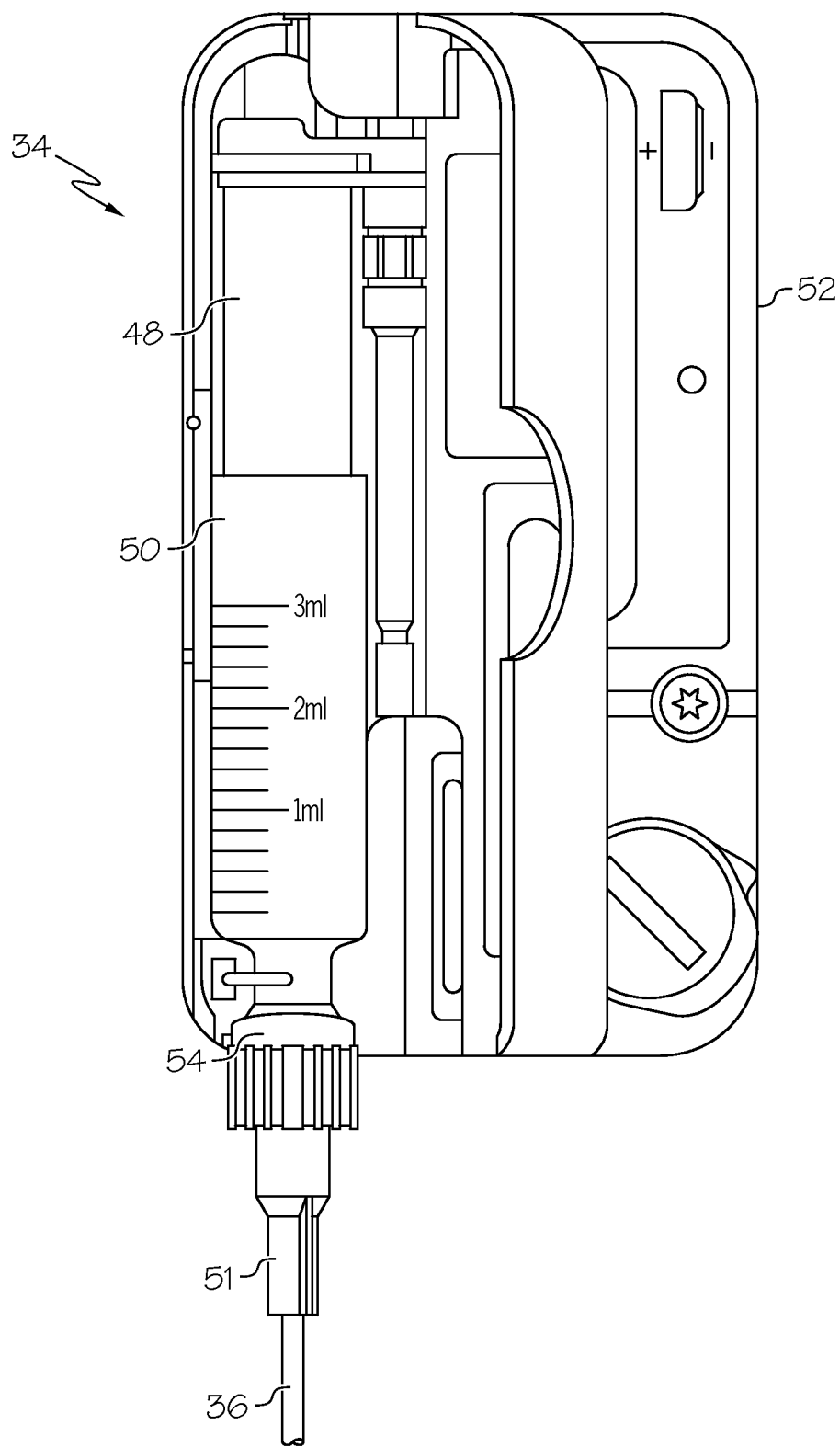
FIG. 5 is a top view of an infusion device with a reservoir door in an open position, for use according to an embodiment.

FIGS. 2-5 illustrate analyte monitoring apparatuses in accordance with certain embodiments. Such analyte monitoring apparatuses may be used, for example, in controlling a patient's glucose level about a target range as discussed above. It should be understood, however, that these are merely examples that may be used for controlling a patient's glucose level about a target range and that claimed subject matter is not limited in this respect. FIG. 2 is a front view of closed loop hardware located on a body in accordance with certain embodiments. FIGS. 3A-3D and 4 show different views and portions of an exemplary analyte monitoring apparatus for use in accordance with certain embodiments. FIG. 5 is a top view of an infusion device with a reservoir door in an open position in accordance with certain embodiments.

Particular embodiments may include a sensor 11, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. As shown in FIGS. 3A and 3B, telemetered characteristic monitor 30 may include a monitor housing 31 that supports a printed circuit board 33, battery or batteries 35, antenna (not shown), a sensor cable connector (not shown), and so forth. A sensing end 40 of sensor 11 may have exposed electrodes 42 that may be inserted through skin 46 to a sensor placement site 44 such as into a subcutaneous tissue of a user's body 20, as shown in FIGS. 3D and 4. Electrodes 42 may be in contact with interstitial fluid (ISF) that is usually present throughout subcutaneous tissue 44.

Sensor 11 may be held in place by sensor set 28, which may be adhesively secured to a user's skin 46, as shown in FIGS. 3C and 3D. Sensor set 28 may provide for a connector end 27 of sensor 11 to connect to a first end 29 of sensor cable 32. A second end 37 of sensor cable 32 may connect to monitor housing 31. A power source 35, such as batteries, that may be included in monitor housing 31 provide power for sensor 11 and electrical components 39 on printed circuit board 33. Electrical components 39 may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 1, 2, and 5, a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucagon may be infused from a reservoir responsive to commands 22 using a similar and/or analogous device (not shown). In alternative implementations, glucose may be administered to a patient orally.

In particular example embodiments, a connector tip 54 of reservoir 50 may extend through infusion device housing 52, and a first end 51 of infusion tube 36 may be attached to connector tip 54. A second end 53 of infusion tube 36 may connect to infusion set 38 (e.g., of FIG. 2). With reference to FIG. 1, insulin 24 may be forced through infusion tube 36 into infusion set 38 and into body 20. Infusion set 38 may be adhesively attached to a user's skin. As part of infusion set 38, a cannula may extend through skin 46 and terminate in subcutaneous tissue 44 to complete fluid communication between a reservoir 50 (e.g., of FIG. 5) and subcutaneous tissue 44 of a user's body 20.

In exemplary alternative embodiments, as pointed out above, a system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Certain examples of system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that may contribute to a sensor measurement lagging behind an actual present value. Also, as noted herein, such a delay may arise from, for instance, a particular level of noise filtering that is applied to a sensor signal. Such delays and/or time lags in obtaining sensor glucose measurements may ultimately affect closed-loop operation. Accordingly, and as discussed in greater detail below, feedback control mechanisms using various approaches by application of a predicted duration of a blood glucose level being outside of a target range to better address a patient's glycemic health.

Figure 6:
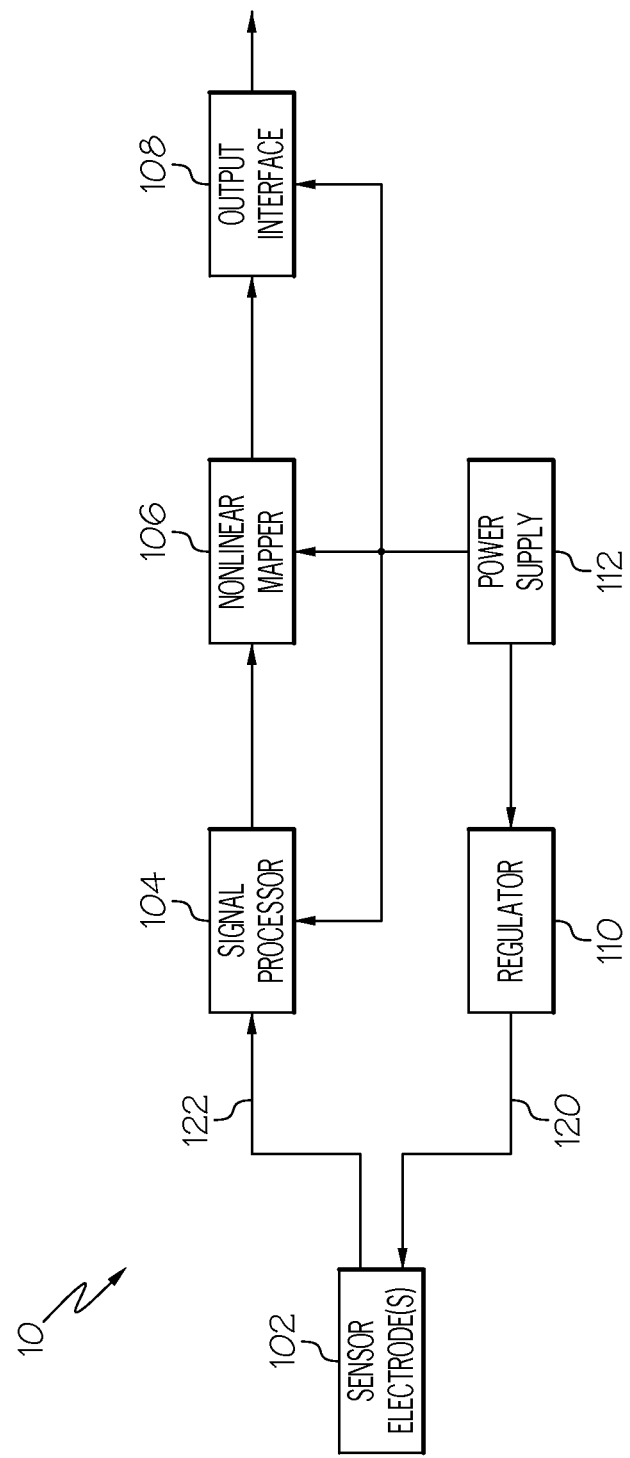
FIG. 6 is a schematic representation of an analyte monitoring apparatus configured in accordance with an embodiment.

FIG. 6 is a schematic representation of an analyte monitoring apparatus 10 configured in accordance with an exemplary embodiment. The monitoring apparatus 10 is suitably configured to measure a physiological characteristic of the subject, e.g., a human patient. In accordance with the non-limiting embodiments presented here, the physiological characteristic of interest is blood glucose, and the monitoring apparatus 10 generates output that is indicative of a blood glucose level of the subject. It should be appreciated that the techniques and methodologies described here may also be utilized with other sensor types if so desired.

FIG. 6 depicts a simplified representation of the monitoring apparatus 10; in practice the monitoring apparatus 10 may include additional elements and functionality that are unrelated or unimportant to the subject matter presented here. Moreover, the monitoring apparatus 10 may incorporate or utilize any of the relevant subject matter that is disclosed in the PCT patent application titled APPLICATION OF ELECTROCHEMICAL IMPEDANCE SPECTROSCOPY IN SENSOR SYSTEMS, DEVICES, AND RELATED METHODS, published Dec. 12, 2013 as International Publication Number WO 2013/184416 A2 (the content of which is incorporated by reference herein).

The illustrated embodiment of the monitoring apparatus 10 generally includes, without limitation: sensor electrodes 102 formed on analyte sensor 11 of FIG. 1; a signal processor 104; a nonlinear mapper 106; an output interface 108; a regulator 110; and a power supply 112. The elements of the monitoring apparatus 10 are coupled together or are otherwise designed to cooperate as needed to support the techniques, methodologies, and operation described in more detail herein. Some or all of the blocks shown in FIG. 6 (e.g., the signal processor 104, the nonlinear mapper 106, and the regulator 110) may include, cooperate with, or be implemented as software, firmware, and/or processing logic. To this end, the monitoring apparatus 10 may include one or more processors and one or more processor-readable storage media having executable instructions stored thereon. The executable instructions, when executed by a processor, are capable of implementing the various methods, processes, and techniques described in more detail below. For example, the nonlinear mapper 106 may be realized using suitably written instructions that perform the desired mapping functions.

The elements depicted in FIG. 6 can be implemented and realized in a variety of different ways, depending on the desired application, device platform, and operating environment. For example, all of blocks illustrated in FIG. 6 could be integrated into a single device or component, such as a glucose sensor device that communicates with a monitor device, an insulin pump device, or a computer. As another example, some of the illustrated blocks (such as the signal processor 104, the nonlinear mapper 106, and the output interface 108) could be implemented in a physically distinct device that communicates with a glucose sensor device that houses the sensor electrodes 102, the regulator, and the power supply 112. These and other implementation and deployment options are contemplated by this disclosure.

The sensor electrodes 102 are designed for subcutaneous placement at a selected site in the body of a user. When placed in this manner, the sensor electrodes 102 are exposed to the user's bodily fluids such that they can react in a detectable manner to the physiological characteristic of interest, e.g., blood glucose level. In certain embodiments, the sensor electrodes 102 may include a counter electrode, a reference electrode, and working electrodes. For the embodiments described here, the sensor electrodes 102 employ thin film electrochemical sensor technology of the type used for monitoring blood glucose levels in the body. Further description of flexible thin film sensors of this general type are found in U.S. Pat. No. 5,391,250, entitled METHOD OF FABRICATING THIN FILM SENSORS, which is herein incorporated by reference. In other embodiments, different types of implantable sensor technology, such as chemical based, optical based, or the like, may be used.

The sensor electrodes 102 cooperate with sensor electronics, which may be integrated with the sensor electrodes 102 in a sensor device package, or which may be implemented in a physically distinct device or component that communicates with the sensor electrodes 102 (such as a monitor device, an infusion pump device, a controller device, or the like). In this regard, any or all of the remaining elements shown in FIG. 6 may be included in the sensor electronics, as needed to support the particular embodiment.

For purposes of this example, the sensor electronics include the signal processor 104, the nonlinear mapper 106, the output interface 108, the regulator 110, and the power supply 112. The power supply 112 provides power (in the form of either a voltage, a current, or a voltage including a current) to the regulator 110. The power supply 112 may also be suitably configured to provide operating power to the signal processor 104, the nonlinear mapper 106, and/or the output interface 108 as needed. In certain embodiments, the power supply 112 is realized using one or more batteries.

The regulator 110 generates and applies regulated voltage to the sensor electrodes 102. In certain embodiments, the regulator 110 applies voltage to the counter electrode of the sensor electrodes 102. The regulator 110 generates and applies DC voltage to the sensor electrodes 102 during a first excitation mode to obtain a constant potential sensor current (Isig) that is indicative of the blood glucose level. The sensor electrodes react to a DC voltage in a way that is influenced by the BG level in the body of the subject. The resulting constant potential sensor current (Isig) serves as the raw sensor output during the DC stimulation mode. Thus, Isig varies in accordance with changes to the BG level of the subject.

In addition, the regulator 110 may generate and apply AC voltage (at different frequencies) to the sensor electrodes 102 during an electrochemical impedance spectroscopy (EIS) excitation mode to carry out an EIS procedure during which EIS output measurements are obtained from the sensor electrodes 102. Thus, the regulator 110 is responsible for managing the excitation voltage characteristics, frequencies, magnitudes, and timing required to support the sensor operating methodologies described herein.

When driven by an excitation voltage signal 120, the sensor electrodes 102 respond in a way that is indicative of a concentration of a physiological characteristic being measured. For this example, the sensor output signal 122 may be indicative of a blood glucose reading. In certain embodiments, the sensor output signal 122 is present at the working electrodes of the sensor electrodes 102. In practice, the sensor output signal 122 may be a current or a voltage measured at the working electrodes. During an EIS procedure, the sensor output signal 122 is indicative of an impedance at the given frequency, an amplitude, and a phase angle.

The signal processor 104 receives the sensor output signals 122 that are produced in response to the application of corresponding DC or AC voltage to the sensor electrodes 102. The signal processor 104 processes the sensor output signals 122 and generates processed sensor signals that are suitable for use as inputs to the nonlinear mapper 106. The nonlinear mapper 106 receives the processed sensor signals and performs a nonlinear mapping operation to generate a corresponding blood glucose value. The nonlinear mapper 106 utilizes a sensor characterization model for the particular type of sensor, wherein the model generates the blood glucose value in the absence of any calibration factor or linear translation. In this regard, the nonlinear mapper 106 is designed and programmed in a way that accurately generates blood glucose values in a calibration-free manner that does not require BG meter (finger stick) measurements. Moreover, the nonlinear mapper 106 is designed and programmed such that the output mapping automatically compensates for typical manufacturing tolerances, shelf life, operating age, and other changes to the monitoring apparatus 10 that would normally be corrected by way of frequent calibration routines.

The BG values generated by the nonlinear mapper 106 may be provided to the output interface 108, which in turn may generate an appropriate output that conveys the BG values. For example, the output interface 108 may include or cooperate with a display driver and graphics processor to render the BG values on a display element (not shown). As another example, the output interface 108 may include or cooperate with a data communication module, such as a network interface, a wireless transmitter, a modem, or the like. The output interface 108 can be designed to support any output format or methodology as appropriate to the particular embodiment. In this regard, the output interface 108 may communicate with any or all of the following, without limitation: a display device; a computer; a pager; a television set; a server; a mobile telephone device; an infusion pump including a display; a personal medical device; hospital equipment; or the like.

Figure 7:
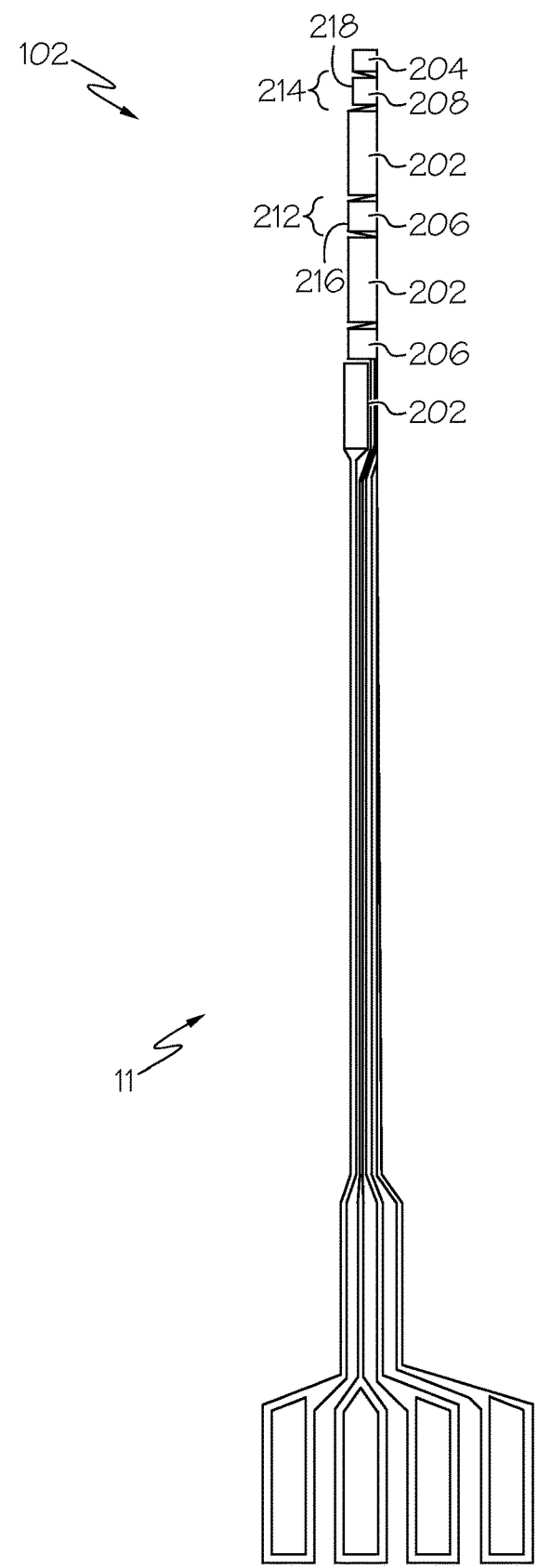
FIG. 7 is a top plan view of an analyte sensor in accordance with an embodiment.

FIG. 7 provides a top plan view of an analyte sensor 11 for use in the monitoring apparatus 10. The analyte sensor 11 includes sensor electrodes 102 that come in contact with blood or interstitial fluid during glucose sensing. In exemplary embodiments, the analyte sensor 11 includes at least one counter electrode 202, at least one reference electrode 204, at least one primary working electrode 206 and at least one auxiliary working electrode 208. The analyte sensor 11 may include more than one of each type of sensor electrode 102. The illustrated analyte sensor 11 includes three counter electrodes 202 and two primary working electrodes 206. Counter electrodes 202 may be provided adjacent each working electrode 206 and 208. Other arrangements of sensor electrodes 102 may be used.

To optimize the electrochemistry of the glucose sensing reaction, in an embodiment the counter electrode 202 is the largest electrode, i.e., has the largest surface area, the working electrodes 206 and 208 are the next largest electrodes and the reference electrode 204 is the smallest electrode. The counter electrode 202 may be as large as possible while consistent with sensor insertion requirements to minimize pain on insertion of the sensor into the body of the user. For instance, to fit within a 22 gauge needle. However, alternative embodiments may be sized to fit other gauge needles ranging from 18 gauge to 30 gauge.

In additional embodiments, the electrodes 102 (i.e., conductors) may have a line width of 50µ to assure good electrical conduction of a sensor signal. However, smaller widths down to 10µ and anything larger can be used if a sufficient signal accuracy is provided and the sensor 102 can fit within a needle as described above.

In exemplary embodiments, the primary working electrode 206 and the auxiliary working electrode 208 have different structures. For example, the primary working electrode 206 may have a first electrochemical surface area 212 and the auxiliary working electrode 208 may have a second electrochemical surface area 214 different from the first electrochemical surface area 212. For example, as shown, the primary working electrode 206 has an outer surface 216 and the auxiliary working electrode 208 has an outer surface 218. In an embodiment, the outer surfaces 216 and 218 may be formed by a same material with substantially identical characteristics. However, the surface areas of the outer surfaces 216 and 218 may differ so that the effective electrochemical surface areas 212 and 214 differ. In an embodiment, the first electrochemical surface area 212 is larger than the second electrochemical surface area 214.

In another embodiment, the outer surfaces 216 and 218 may be formed by different materials or by a same material having different characteristics. For example, outer surface 216 may be formed rougher, i.e., with greater height and depth changes, than outer surface 218. Thus, the two-dimensional cross sectional areas of the primary working electrode 206 and the auxiliary working electrode 208 may be substantially equal, while the first electrochemical surface area 212 may be larger than the second electrochemical surface area 214.

In accordance with an embodiment herein, the primary working electrode 206 and the auxiliary working electrode 208 are each provided to sense a blood glucose level at the sensor placement site. However, the primary working electrode 206 and the auxiliary working electrode 208 are adapted to provide different responses to certain physiological characteristics at the sensor placement site.

Figure 8:
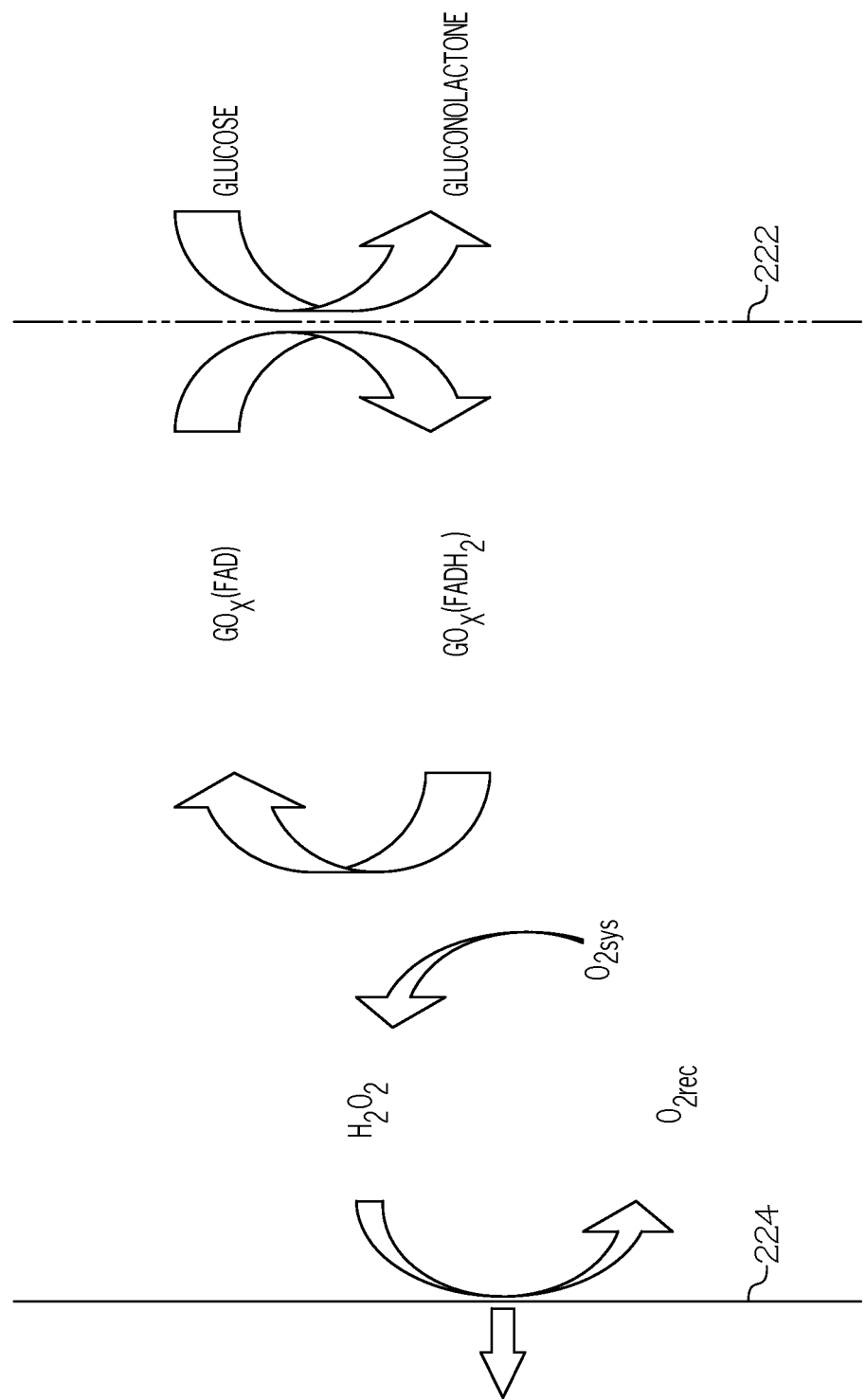
FIG. 8 is a schematic illustration of the glucose sensing mechanism of an analyte sensor in accordance with an embodiment.

FIG. 8 provides a schematic illustration of the glucose sensing mechanism of a working electrode 206 or 208. As noted above, the glucose sensing reaction of equation 1 requires oxygen. In FIG. 1, glucose binds to a glucose oxidase enzyme (GOx) and flavin adenine dinucleotide (FAD) cofactor (GOx-FAD) immobilized on the sensor surface 222. FAD works as the initial electron acceptor and is reduced to GOx-FADH$_2$. Then FADH$_2$ is oxidized by the final electron acceptor, molecular oxygen ($O_{2sys}$), which can do so because oxygen has a higher reduction potential. The oxygen is provided in the tissue at the sensor placement site.

Oxygen is then reduced to hydrogen peroxide ($H_2O_2$). The hydrogen peroxide is further oxidized at the electrode surface 224, such as a platinum (Pt) surface, donating electrons to the electrode and in the process evolving oxygen ($O_{2rec}$) as a byproduct.

Thus, the reaction includes the steps of:
Step 1: $H_2O_2 + Pt(OH) \leftrightarrow Pt(OH)*(H_2O_2)$
Step 2: $Pt(OH)*(H_2O_2) \rightarrow Pt + 2H_2O + O_2$
Step 3: $Pt + 2H_2O \rightarrow Pt(OH) + 2H^- + e^-$ As can be seen, the reaction is mass transfer limited, and all the available hydrogen peroxide is immediately oxidized at the electrode surface 224.

Embodiments herein provide the primary working electrode 206 and the auxiliary working electrode 208 with different electrochemical surface areas in order to identify changes in the oxygen level at the sensor placement site. Specifically, for a working electrode with a smaller electrochemical surface area, e.g., the auxiliary working electrode 208, the hydrogen peroxide oxidation reaction step at the electrode surface 218 is more kinetically controlled. In other words, at any given concentration of hydrogen peroxide, less hydrogen peroxide gets oxidized at the electrode surface 218 as compared to the amount of hydrogen peroxide that is oxidized at the electrode surface, e.g., surface 216, of a working electrode having a higher electrochemical surface area, e.g., primary working electrode 206. Thus, a reduction in the tissue oxygen leads to disturbance of the steady flux of hydrogen peroxide from the enzyme layer to the electrode layer.

For the primary working electrode 206 with a higher electrochemical surface area, the amount of evolved oxygen ($O_{2rec}$) is reasonably high to sustain the Isig generation momentarily after a decrease in tissue oxygen. The dearth of $O_{2sys}$ (due to the low oxygen environment) and availability of transient $O_{2rec}$ causes the Glucose→$H_2O_2$ reaction to shift closer to the electrode surface. This in turn causes the hydrogen peroxide flux to increase momentarily causing the Isig to increase before the Isig gradually dips.

In contrast, at the auxiliary working electrode 208 with a lower electrochemical surface area, there is less or no available evolved oxygen ($O_{2rec}$). Thus, the reduction in tissue oxygen leads to an immediate and significant reduction in hydrogen peroxide. With no mechanism to generate more hydrogen peroxide, the Isig will dip instantly. Thus, the auxiliary working electrode becomes highly sensitive to decreases in oxygen.

In summary, if the Isig for the primary working electrode 206 starts increasing and the Isig for the auxiliary working electrode 208 starts rapidly decreasing, the onset of a decline in tissue oxygen is detected at the sensor placement site (local hypoxia).

Figure 9:
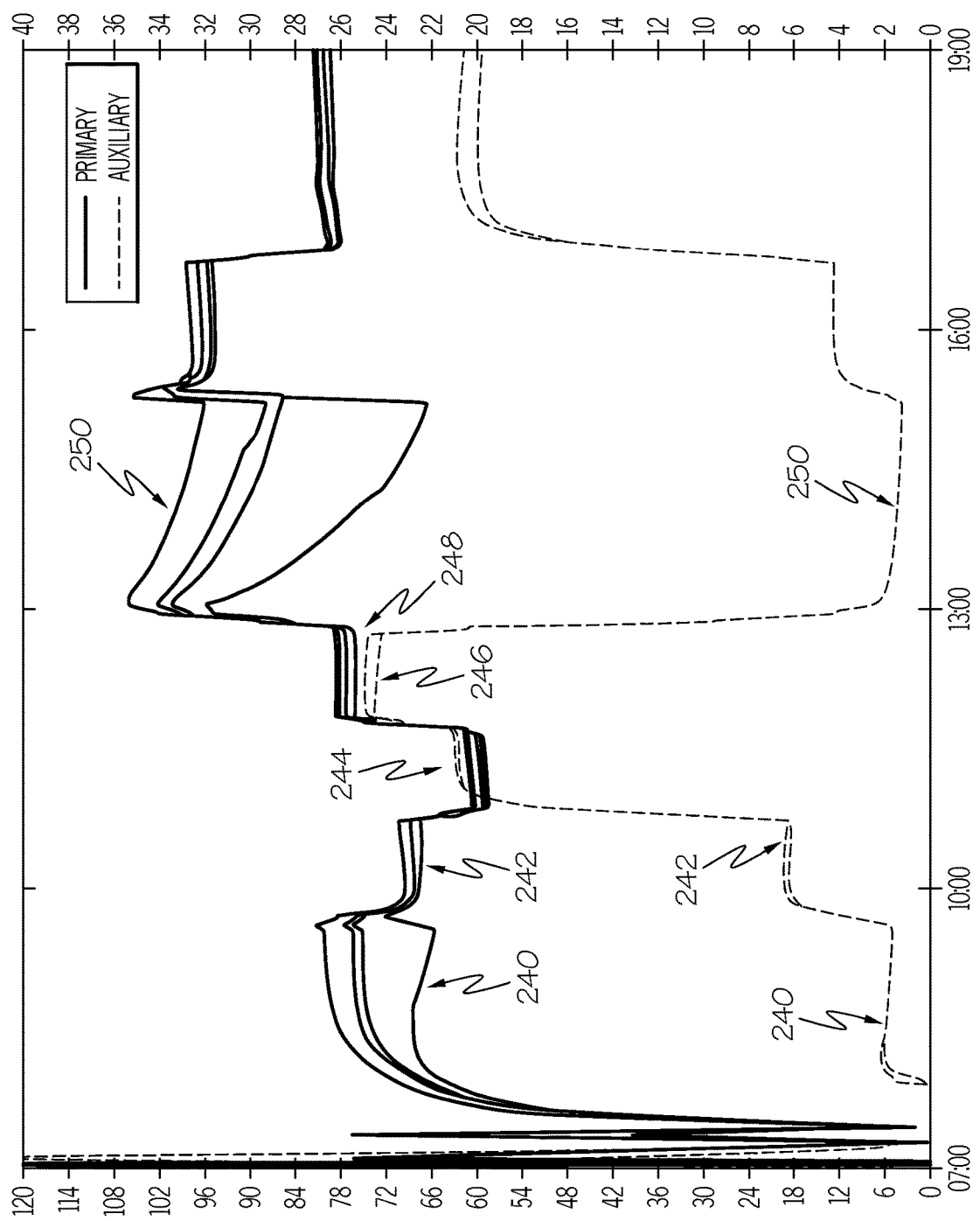
FIG. 9 is a graph illustrating the constant potential sensor current (Isig) for working electrodes having different structures in accordance with an embodiment.

FIG. 9 is a graph illustrating the Isig for a primary working electrode provided with a higher electroactive surface area and for an auxiliary working electrode provided with a lower electroactive surface area. Time is recorded on the x-axis in seconds and the Isig value is recorded on the y-axis, with the primary working electrode Isig indicated by the numbering on the left side of the graph (from 0 to 120 nA) and the auxiliary working electrode Isig indicated by the numbering on the right side of the graph (from 0 to 40 nA).

At the time indicated by arrows 240, the glucose level is 300 mg/dL and the oxygen level is 0.1%. The recorded Isig values are appropriate for the relative sensor size. At the time indicated by arrows 242, the glucose level is 300 mg/dL and the oxygen level has risen to 1%. At the time indicated by arrows 244, the glucose level is 300 mg/dL and the oxygen level has risen to 5%. The signal change from time 240 to time 242 to time 244 indicates the increase in system oxygen, as the in vivo environment becomes conducive to glucose sensing. In practice, this signal change can indicate the entrance into an unreliable glucose in vivo sensing phase. At the time indicated by arrows 246, the glucose level has risen to 400 mg/dL and the oxygen level remains at 5%. At the time indicated by arrow 248, the oxygen level provided is reduced to 0.1%. This change in oxygen level causes an easily recognized change in Isig from the two sensors.

As may be seen, the Isig recorded by the auxiliary electrode immediately drops in response to the decreasing oxygen level. On the other hand, the Isig recorded by the primary working electrode temporarily increases in response to the decreasing oxygen level. At the time indicated by arrows 250, the glucose level is 400 mg/dL and the oxygen level has fallen to 0.1%. The signal change from time 246 to time 248 to time 250 indicates the decrease in system oxygen, as the in vivo environment become non-conducive to glucose sensing. This signal change can indicate the return of the sensor to a reliable glucose in vivo sensing phase.

As shown by FIG. 9, the primary and auxiliary working electrodes exhibit different responses to the decrease in the oxygen level. The primary signal increases in response to the decrease in tissue oxygen while the auxiliary signal decreases in response to the decrease in tissue oxygen. The differences in response may be recognized by the controller 12 as indicative of a low oxygen environment. Further, such responses may be exhibited by sensors 206 and 208 that utilize the same glucose sensing mechanism, albeit with structural differences, i.e., different electrochemical surface areas.

The power source may supply a same operating voltage to the primary working electrode 206 and the auxiliary working electrode 208. Alternatively, the power source may supply different operating voltages to the primary and auxiliary working electrodes. The primary working electrode 206 and auxiliary working electrode 208 may have an identical structure except for the difference in electrochemical surface area. For example, each working electrode 206 and 208 may have the structure 300 illustrated in FIG. 10.

Figure 10:
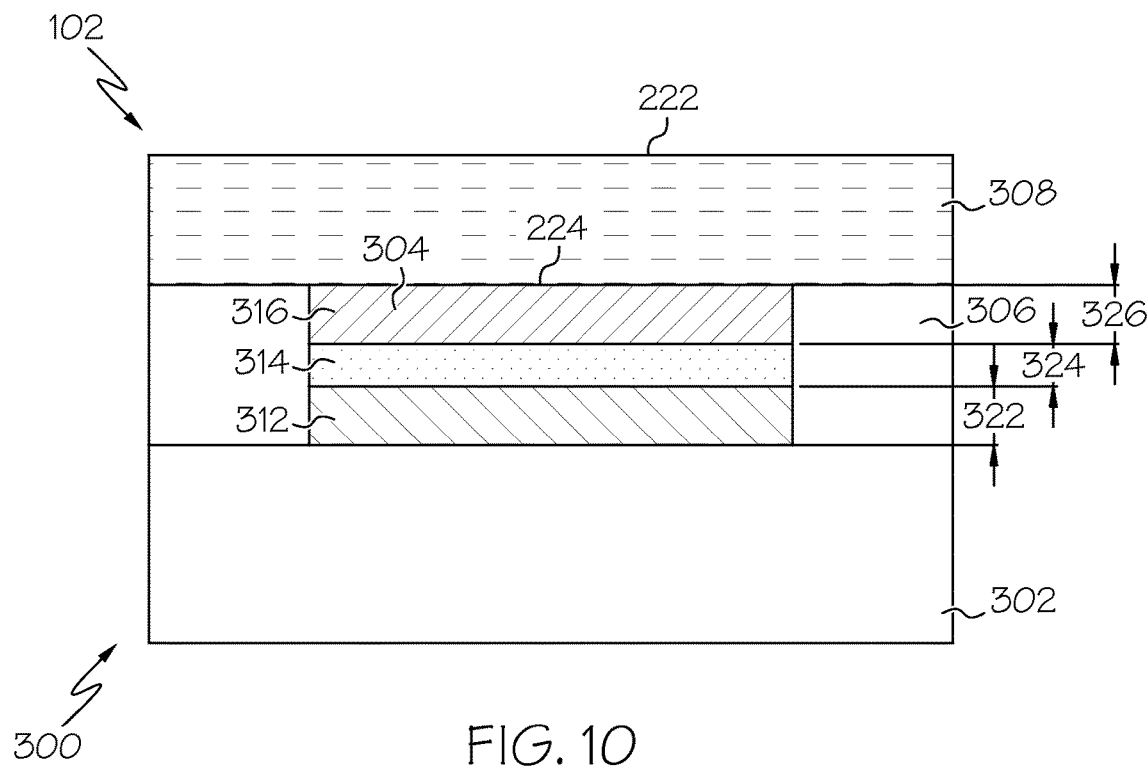
FIG. 10 is a diagrammatic view of a layered working electrode configuration in accordance with an embodiment.

FIG. 10 illustrates a cross-section of an exemplary sensor electrode 102. The sensor electrode 102 is formed from a plurality of components that are typically in the form of layers of various conductive and non-conductive constituents disposed on each other according to art accepted methods. The components of the sensor electrode 102 are typically characterized herein as layers because, for example, it allows for a facile characterization of the sensor structure 300. Artisans will understand however, that in certain embodiments, the sensor constituents are combined such that multiple constituents form one or more heterogeneous layers. In this context, those of skill in the art understand that the ordering of the layered constituents can be altered in various embodiments.

The embodiment shown in FIG. 2 includes a base layer 302 to support the sensor electrode 102. The base layer 302 can be made of a material such as a metal and/or a ceramic and/or a polymeric substrate, which may be self-supporting or further supported by another material as is known in the art. The base layer 302 may be a polymer, such as non-toxic biocompatible polymers such as silicone compounds, polyimides, biocompatible solder masks, epoxy acrylate copolymers, or the like. An exemplary base layer 302 is a polyimide.

The exemplary sensor electrode 102 includes conductive layers 304 which are disposed on and/or combined with the base layer 302. The base layer 302 and/or conductive layers 304 can be generated using many known techniques and materials. In certain embodiments, the electrical circuit of the sensor is defined by etching the disposed conductive layer 304 into a desired pattern of conductive paths. An electrically insulating layer 306 is formed around the conductive layers 304. For example, the electrically insulating layer 306 may be a polymer coating, such as non-toxic biocompatible polymers such as silicone compounds, polyimides, biocompatible solder masks, epoxy acrylate copolymers, or the like.

As shown, the conductive layers 304 are exposed through the insulating layer 306 to open the conductive layers 304 to the external environment and to, for example, allow an analyte such as glucose to permeate the layers of the sensor electrode 102 and be sensed by the sensing elements. Specifically, the conductive layers 304 include an electrode surface 224 on which hydrogen peroxide may be oxidized as described above.

In the configuration shown in FIG. 10, an analyte sensing layer 308 (which is typically a sensor chemistry layer, meaning that materials in this layer undergo a chemical reaction to produce a signal that can be sensed by the conductive layers) is disposed on the exposed electrode surface 224. The analyte sensing layer 308 forms the sensor surface 222 where an analyte such as glucose may bind as described above. Typically, the analyte sensing layer 308 is an enzyme layer. Most typically, the analyte sensing layer 308 includes an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 308 reacts with glucose to produce hydrogen peroxide, a compound which then modulates a current at the electrode surface 224. As this modulation of current depends on the concentration of hydrogen peroxide, and the concentration of hydrogen peroxide correlates to the concentration of glucose, the concentration of glucose can be determined by monitoring this modulation in the current. In a specific embodiment, the hydrogen peroxide is oxidized at an electrode surface 224 that is an anode (also termed herein the anodic electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments, the analyte sensing layer 308 can be applied over portions of the conductive layers or over the entire region of the conductive layers. Typically the analyte sensing layer 308 is disposed on the working electrode which can be the anode or the cathode. Optionally, the analyte sensing layer 308 is also disposed on a counter and/or reference electrode. While the analyte sensing layer 308 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. Some methods for generating a thin analyte sensing layer 308 include brushing the layer onto a substrate (e.g. the reactive surface of a platinum black electrode), as well as spin coating processes, dip and dry processes, low shear spraying processes, ink jetprinting processes, silk screen processes and the like. In certain embodiments, brushing is used to: (1) allow for a precise localization of the layer; and (2) push the layer deep into the architecture of the reactive surface of an electrode (e.g. platinum black produced by an electrodeposition process).

Typically, the analyte sensing layer 308 is coated and or disposed next to one or more additional layers. Optionally, the one or more additional layers include a protein layer disposed upon the analyte sensing layer 308. Typically, the protein layer includes a protein such as human serum albumin, bovine serum albumin or the like. In some embodiments, an additional layer includes an analyte modulating layer that is disposed above the analyte sensing layer 308 to regulate analyte contact with the analyte sensing layer 308. For example, the analyte modulating membrane layer can include a glucose limiting membrane, which regulates the amount of glucose that contacts an enzyme such as glucose oxidase that is present in the analyte sensing layer 308. Such glucose limiting membranes can be made from a wide variety of materials known to be suitable for such purposes, e.g., silicone compounds such as polydimethyl siloxanes, polyurethanes, polyurea cellulose acetates, Nafion, polyester sulfonic acids (e.g. Kodak AQ), hydrogels or any other suitable hydrophilic membranes known to those skilled in the art.

In certain embodiments, an adhesion promoter layer is disposed between the analyte modulating layer and the analyte sensing layer 308 in order to facilitate their contact and/or adhesion. For example, an adhesion promoter layer may be disposed between the analyte modulating layer and the protein layer in order to facilitate their contact and/or adhesion. The adhesion promoter layer can be made from any one of a wide variety of materials known in the art to facilitate the bonding between such layers. Typically, the adhesion promoter layer includes a silane compound. In alternative embodiments, protein or like molecules in the analyte sensing layer 308 can be sufficiently crosslinked or otherwise prepared to allow the analyte modulating membrane layer to be disposed in direct contact with the analyte sensing layer 308 in the absence of an adhesion promoter layer. In certain embodiments, additional layers such as an interference rejection layer may be included in the sensor 102.

In an exemplary embodiment, the conductive layers 304 include a first conductive layer 312, such as a metal layer. The first conductive layer 312 may be deposited on the base layer 302 by a deposition process such as sputtering. Sputtering can be carried out using commercially available sputtering reactors using an RF (radio frequency). Magnetron sputtering can also be used. Magnetron sputtering uses a magnetic field to concentrate electrons near the target surface to increase the deposition rate. Other known deposition processes, such as chemical vapor deposition (CVD) methods, can also be employed. The thickness of an exemplary deposited layer ranges from about 0.05µ to about 300.0µ, such as about 0.5µ to about 25.0µ. When multiple layers are deposited, the total thickness of the layers may have a thickness within the foregoing ranges.

A second conductive layer 314, such as a metal layer, may be formed over the first conductive layer 312. For example, the second conductive layer 314 may be deposited by a sputtering process or by other known deposition processes as described in relation to the deposition of the first conductive layer 312.

Exemplary metal layers for forming layers 312 and 314 include, without limitation, elemental metals such as chromium, gold, copper, aluminum, nickel, tantalum and titanium, alloys such as Inconel and Nichrome, and mixtures thereof. The term "metal layer" is also intended to encompass layers that include one or more non-metallic elements in a mixture or chemical combination with one or more metallic elements, and thus also encompasses materials such as oxides, for example alumina. Reactive as well as non-reactive layers can be formed; reactive materials, such as tantalum oxide, chromium oxide, etc., are also intended to be encompassed by the term "metal layer." Specific combinations of metal layers that are useful include chromium and copper; copper and gold; and chromium, gold and chromium; copper, nickel and gold; and chromium, copper, nickel and gold.

In particular embodiments, chromium forms the first sputtered metal layer 312. Chromium provides an additional benefit in promoting adhesion between certain polymeric materials, such as polyimides, and other metals. Other metal layers, such as nickel or the like, that promote adhesion can also be employed if desired. In particular embodiments, gold forms the second sputtered metal layer 314.

As shown in FIG. 10, a third conductive layer 316, such as a metal layer, is formed over layers 312 and 314. An exemplary third conductive layer 316 is plated on the uppermost sputtered metal layer. Such layers, in exemplary embodiments, are platinum. However, in alternative embodiments, other metals, such as copper, nickel, iridium, chromium, gold, or the like, may be plated onto the layers used to form the sensor electrode 102.

In FIG. 10, conductive layer 312 is formed with a thickness 322 of from about 50 Å to about 800 Å, conductive layer 314 is formed with a thickness 324 of from about 3000 Å to about 20,000 Å, and conductive layer 316 is formed with a thickness 326 of from about 5000 Å to about 40,000 Å.

Figure 11:
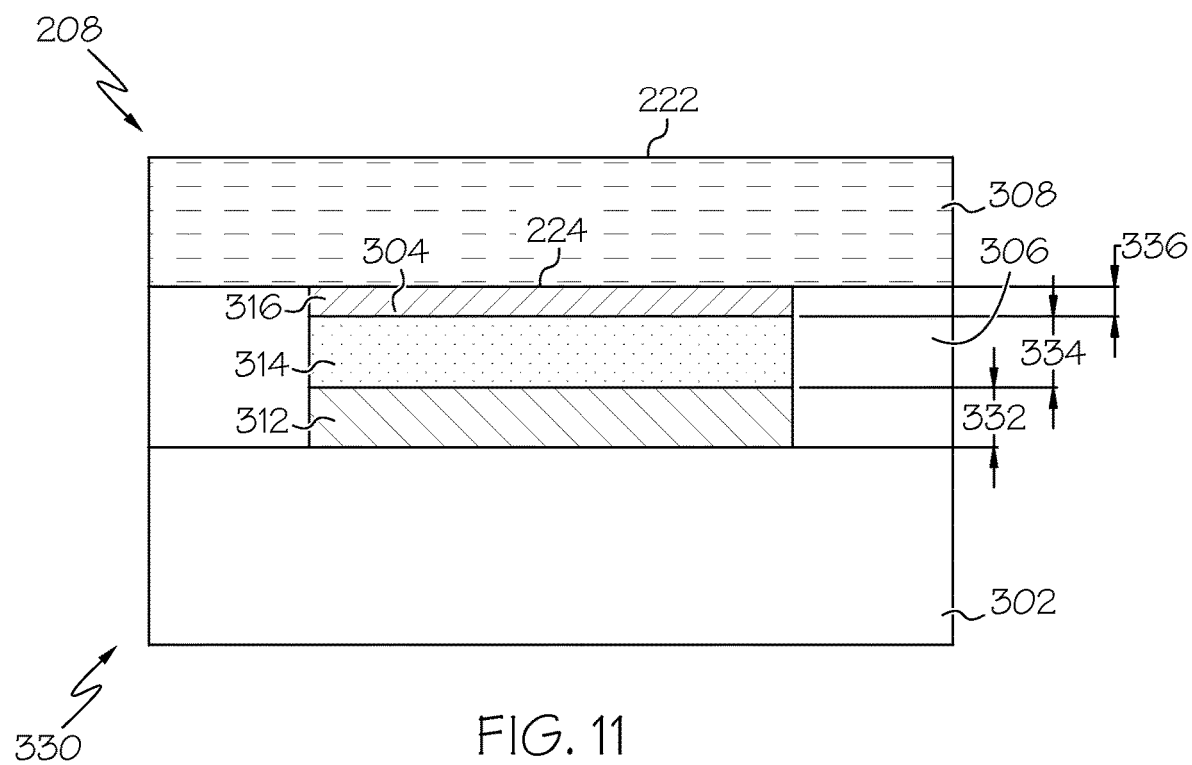
FIG. 11 is a diagrammatic view of a layered auxiliary working electrode configuration in accordance with an embodiment.

In certain embodiments, the primary working electrode 206 may have the structure 300 of the sensor electrode 102 in FIG. 10 and the auxiliary working electrode 208 may have a different structure 330 as shown in FIG. 11. The structure 330 of auxiliary working electrode 208 includes conductive layers 312, 314 and 316 having different thickness than in the structure 300 of FIG. 10. For example, in FIG. 11, conductive layer 312 is formed with a thickness 332 of about 50 Å to about 800 Å, conductive layer 314 is formed with a thickness 334 of about 3000 Å to about 20,000 Å, and conductive layer 316 is formed with a thickness 336 of about 50 Å to about 15,000 Å. The difference in thickness of layer 316 results in large difference in electrochemical surface area (a thicker layer can have a larger electrochemical surface area assuming the layers are plated using the same plating technique) between structure 300 of FIG. 10 and structure 330 of FIG. 11. The materials of the structure 330 may be identical to or different from the materials of the structure 300.

In the embodiments described above, the auxiliary working electrode 208 monitors glucose levels in the same manner as the primary working electrode 206. Through the different responses in signals from the primary working electrode 206 and the auxiliary working electrode 208 produced by a change in oxygen at the sensor placement site, changes in oxygen levels are identified. Such changes may be used to temporarily disregard or further investigate blood glucose measurements by the electrodes 206 and 208 when a decrease in tissue oxygen is indicated.

Figure 12:
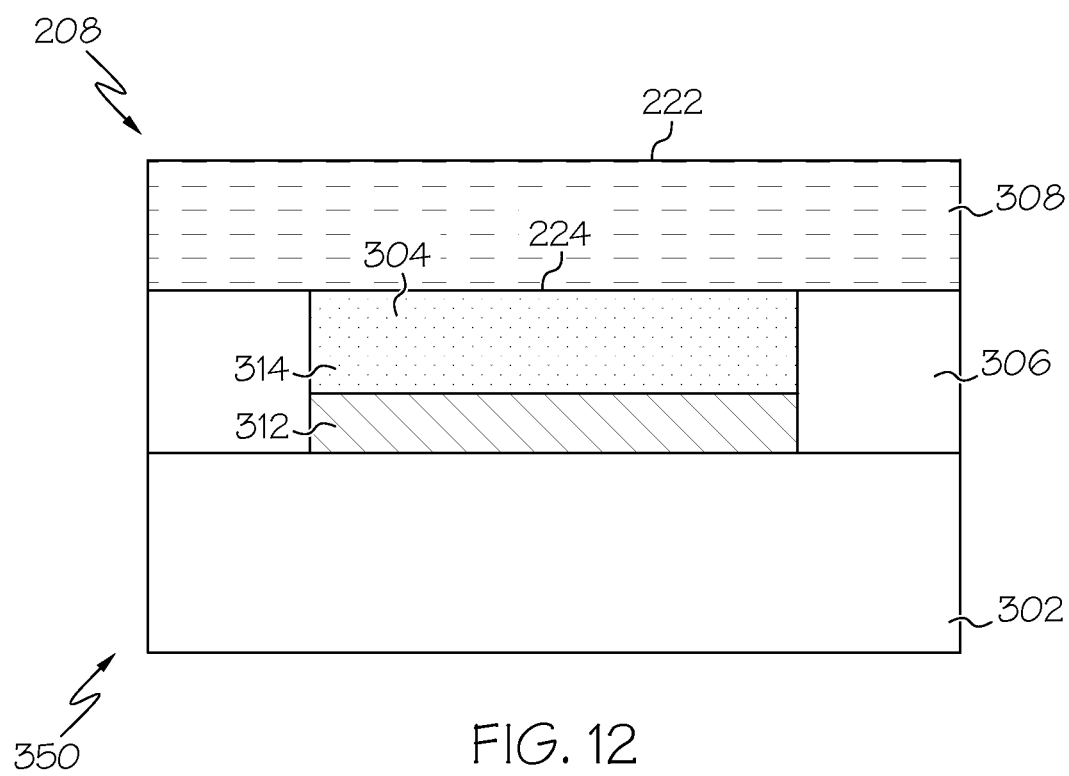
FIG. 12 is a diagrammatic view of a layered auxiliary working electrode configuration in accordance with an embodiment.
Figure 13:
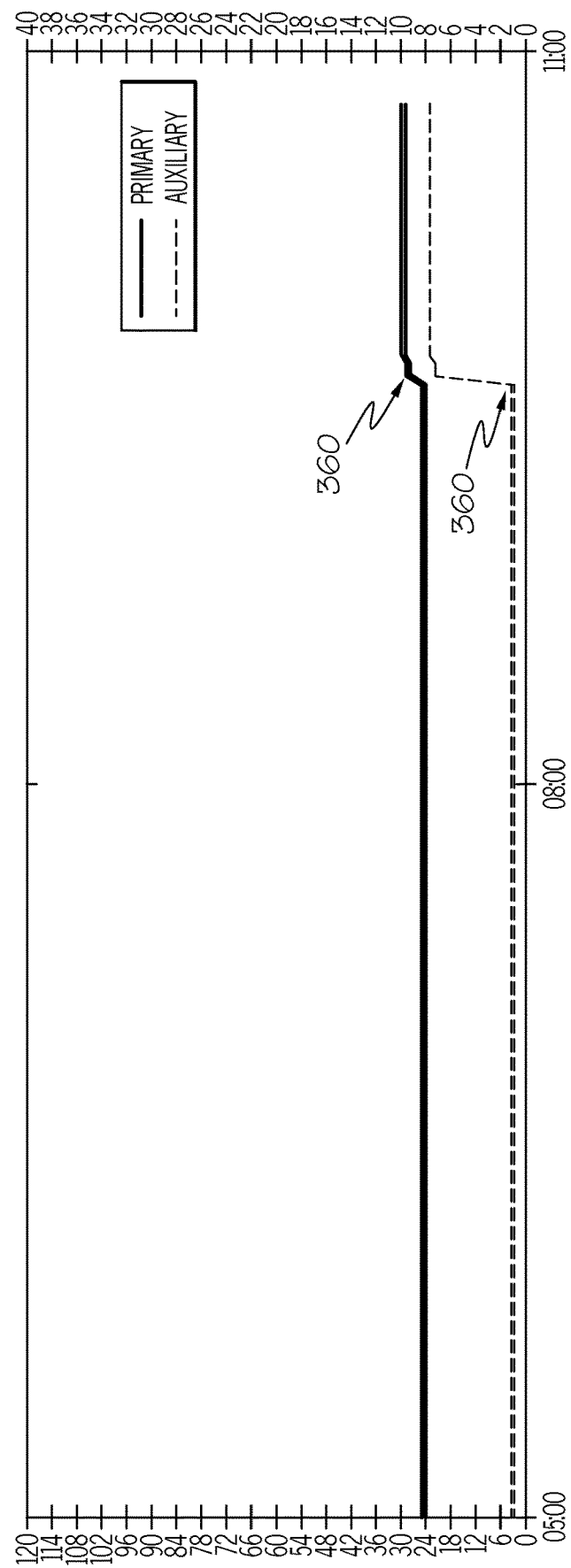
FIG. 13 is a graph illustrating the constant potential sensor current (Isig) for a glucose monitoring primary working electrode and an interferent monitoring auxiliary working electrode in accordance with an embodiment.

FIGS. 12-13 illustrate another embodiment of the auxiliary electrode 208. As noted above, the primary working electrode 206 is sensitive to electroactive interferents. Presence of an electroactive interferent, such as acetaminophen, in vivo near the sensor placement site can cause gradual or incisive transgression towards an unsuitable glucose sensing environment. As a result, issues like Isig dips, sensor sensitivity less, and false sensor glucose over-reading (increased Isig in response to presence of acetaminophen) may occur.

In the embodiment of FIGS. 12-13, the auxiliary working electrode 208 does not monitor blood glucose levels. Rather, the auxiliary working electrode 208 is provided with the diagnostic capability to detect transient incisive but false increase in sensor glucose value due to introduction of electroactive interferents. Specifically, the auxiliary working electrode 208 monitors electroactive interferent concentration at the sensor placement site. The auxiliary working electrode 208 may provide a signal indicative of measurements of an electroactive interferent at the sensor placement site.

In FIG. 12, the auxiliary working electrode 208 has a structure 350. The structure 350 of the auxiliary working electrode 208 includes the base layer 302, conductive layers 304, electrically insulating layer 306, and analyte sensing layer 308. However, as shown, the conductive layers 304 include only the sputtered layers 312 and 314. The plated layer 316 is not present in the structure 350 of FIG. 12.

The materials used in each of the components of structure 350 may be the same as in the structures 300 and 330. For example, the sputtered layer 312 may be chromium and the sputtered layer 314 may be gold.

As the electrode surface 224 is formed by sputtered layer 314 rather than the plated layer 316 of structures 300 and 330, the auxiliary working electrode 208 in FIG. 12 is much more sensitive to interferents than to glucose. For example, any perturbation at the sensor placement site with an injection of glucose (up to 400 mg/dL) does not evoke a strong Isig response from the auxiliary working electrode 208 of FIG. 12.

FIG. 13 illustrates the behavior of the auxiliary working electrode 208 of FIG. 12 and a primary working electrode 206 as described in prior embodiments. FIG. 13 is a graph illustrating the Isig for a primary working electrode provided with an electrode surface formed by a plated metal layer for monitoring glucose levels, and the Isig for an auxiliary working electrode provided with an electrode surface formed by a sputtered metal layer for monitoring interferent levels. Time is recorded on the x-axis in hour:minutes and the Isig value is recorded on the y-axis, with the primary working electrode Isig indicated by the numbering on the left side of the graph (from 0 to 120 nA) and the auxiliary working electrode Isig indicated by the numbering on the right side of the graph (from 0 to 40 nA).

At the time indicated by arrows 360, 0.1 mg/dL of acetaminophen at 100 mg/dL glucose is injected at the sensor placement site. As a result, an approximately 800% increase in Isig is recorded by the auxiliary working electrode. On the other hand, a 15-20% increase in Isig is recorded by the primary working electrode. Thus, the response by the auxiliary working electrode is at least about 5 times larger, such as at least about 10 times larger, for example at least about 20 times larger, than the response by the primary working electrode. More specifically, the response by the auxiliary working electrode is at least about 30 times larger, such as about 40 times larger, than the response by the primary working electrode. The response of the auxiliary working electrode may be easily recognized as an indication of an increase in electroactive interferents at the sensor placement site.

Thus, the auxiliary working electrode 208 of FIGS. 12-13 is able to monitor the presence of electroactive interferents at the sensor placement site. An analyte monitoring apparatus including a primary working electrode for monitoring glucose and an auxiliary working electrode for monitoring electroactive interferents may characterize an increase in an electroactive interferent and temporarily disregard or further investigate blood glucose measurements otherwise indicating an increase in glucose levels.

Unless specifically stated otherwise, as is apparent from the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device or apparatus may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular embodiments, such a special purpose computer or similar may include one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above apparatuses, methods, sensors, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may include one or more storage articles and/or devices for storing machine-readable instructions or information. Such storage articles and/or devices may include any one of several non-transitory media types including, for example, magnetic, optical, semiconductor, a combination thereof, or other storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method for monitoring an analyte within the body of a patient, the method comprising:
    implanting an analyte sensor at a sensor placement site in the patient, the analyte sensor comprising: a reference electrode; a counter electrode; at least one primary working electrode having a first electrochemical surface area; and at least one auxiliary working electrode having a second electrochemical surface area less than the first electrochemical surface area;
    communicating a primary constant potential sensor current (primary Isig) from the at least one primary working electrode and an auxiliary constant potential sensor current (auxiliary Isig) from the at least one auxiliary working electrode to a processor, wherein the primary Isig and the auxiliary Isig are analyte dependent;
    monitoring a level of the analyte in the body of the patient based on the primary Isig and the auxiliary Isig;
    identifying an increase in the primary Isig as a result of a decline in oxygen at the sensor placement site;
    simultaneous with the increase in the primary Isig, identifying a decrease in the auxiliary Isig as a result of the decline in oxygen at the sensor placement site;
    detecting the onset of the decline in oxygen at the sensor placement site in response to the increase in the primary Isig and the simultaneous decrease in the auxiliary Isig; and
    further investigating the primary Isig in response to detecting the onset of the decline in oxygen at the sensor placement site.

2. The method of claim 1 further comprising characterizing an increase in electroactive interferent concentration at the sensor placement site in response to the increase in the primary Isig and the decrease in the auxiliary Isig.

3. The method of claim 1 wherein the at least one primary working electrode is adapted to have a first response to an electroactive interferent, wherein the at least one auxiliary working electrode is adapted to have a second response to the electroactive interferent different from the first response.

4. The method of claim 1 wherein each of the at least one primary working electrode and the at least one auxiliary working electrode includes a deposited metal layer, wherein the deposited metal layer forms an outer surface of the at least one auxiliary working electrode, and wherein the at least one primary working electrode includes a plated metal layer that is plated on the deposited metal layer and that forms an outer surface of the at least one primary working electrode.

5. The method of claim 1 further comprising supplying a same operating voltage to the at least one primary working electrode and the at least one auxiliary working electrode.

6. The method of claim 1 further comprising supplying different operating voltages to the at least one primary working electrode and the at least one auxiliary working electrode.

7. A method for monitoring an analyte within the body of a patient, the method comprising:
    implanting an analyte sensor at a sensor placement site in the patient, the analyte sensor comprising: a reference electrode; a counter electrode; at least one primary working electrode having a first electrochemical surface area; and at least one auxiliary working electrode having a second electrochemical surface area different from the first electrochemical surface area;
    providing measurements of glucose levels at the sensor placement site in a primary constant potential sensor current (primary Isig) from the at least one primary working electrode;
    providing measurements of an electroactive interferent at the sensor placement site in an auxiliary constant potential sensor current (auxiliary Isig) from the at least one auxiliary working electrode;
    communicating the primary Isig and the auxiliary Isig to a processor wherein the primary Isig and the auxiliary Isig are analyte dependent;
    monitoring the primary Isig to identify changes in glucose levels at the sensor placement site; and
    monitoring the auxiliary Isig with the processor and comparing simultaneous measurements of the auxiliary Isig and the primary Isig to identify an increase in the electroactive interferent and to further investigate the primary Isig when the primary Isig increases and the auxiliary Isig decreases as a result of the decline in oxygen at the sensor placement site.

8. The method of claim 7 wherein monitoring the primary Isig and the auxiliary Isig comprises sensing alterations in the primary Isig from the at least one primary working electrode and the auxiliary Isig from the at least one auxiliary working electrode.

9. The method of claim 7 wherein the at least one primary working electrode is adapted to have a first response to the electroactive interferent, wherein the at least one auxiliary working electrode is adapted to have a second response to the electroactive interferent different from the first response.

10. The method of claim 7 wherein each of the at least one primary working electrode and the at least one auxiliary working electrode includes a deposited metal layer, wherein the deposited metal layer forms an outer surface of the at least one auxiliary working electrode, and wherein the at least one primary working electrode includes a plated metal layer that is plated on the deposited metal layer and that forms an outer surface of the at least one primary working electrode.

11. The method of claim 1 further comprising supplying a same operating voltage to the at least one primary working electrode and the at least one auxiliary working electrode.

12. The method of claim 1 further comprising supplying different operating voltages to the at least one primary working electrode and the at least one auxiliary working electrode.

* * * * *